United States Patent [19]

Nakamori et al.

[11] Patent Number: 5,405,521
[45] Date of Patent: Apr. 11, 1995

[54] OXYGEN CONCENTRATION MEASURING DEVICE

[75] Inventors: Yasutaka Nakamori, Anjo; Tomomichi Mizoguchi, Nagoya; Shigenori Isomura, Kariya; Toshihiro Suzumura, Nagoya, all of Japan

[73] Assignee: Nippondenso Co., Ltd., Kariya, Japan

[21] Appl. No.: 160,094

[22] Filed: Dec. 1, 1993

[30] Foreign Application Priority Data

Dec. 2, 1992 [JP] Japan .................................. 4-323213
Sep. 1, 1993 [JP] Japan .................................. 5-217751
Oct. 1, 1993 [JP] Japan .................................. 5-247054

[51] Int. Cl.⁶ .......................................... G01N 27/26
[52] U.S. Cl. .................................. 204/425; 204/406; 204/408; 204/427; 204/429
[58] Field of Search ............... 204/406, 408, 425, 426, 204/427, 429; 123/676, 693, 694, 697, 704

[56] References Cited

U.S. PATENT DOCUMENTS 4,543,176 9/1985 Harada et al. ...................... 204/406

FOREIGN PATENT DOCUMENTS 57-192852 11/1982 Japan .
59-163556 9/1984 Japan .
60-125553 7/1985 Japan .
60-202351 10/1985 Japan .
125419 5/1989 Japan .
128905 6/1989 Japan .

Primary Examiner—John Niebling
Assistant Examiner—Bruce F. Bell
Attorney, Agent, or Firm—Cushman, Darby & Cushman

[57] ABSTRACT

An oxygen concentration measuring device capable of significantly shortening the period of time during which oxygen concentration cannot be measured. When measuring the temperature of a sensor main body, a microcomputer determines the temperature of the sensor main body by estimating a saturation current starting from a current detected by a current detecting circuit in a period of time before current flowing through the sensor main body finishes rising, after the sensor main body has been negatively biased by a bias control circuit. The sensor main body is positively biased by the bias control circuit directly after the period of time has lapsed. The microcomputer determines an air fuel ratio by using current in a period of time before current flowing through the sensor main body due to the positive bias finishes decreasing.

13 Claims, 19 Drawing Sheets

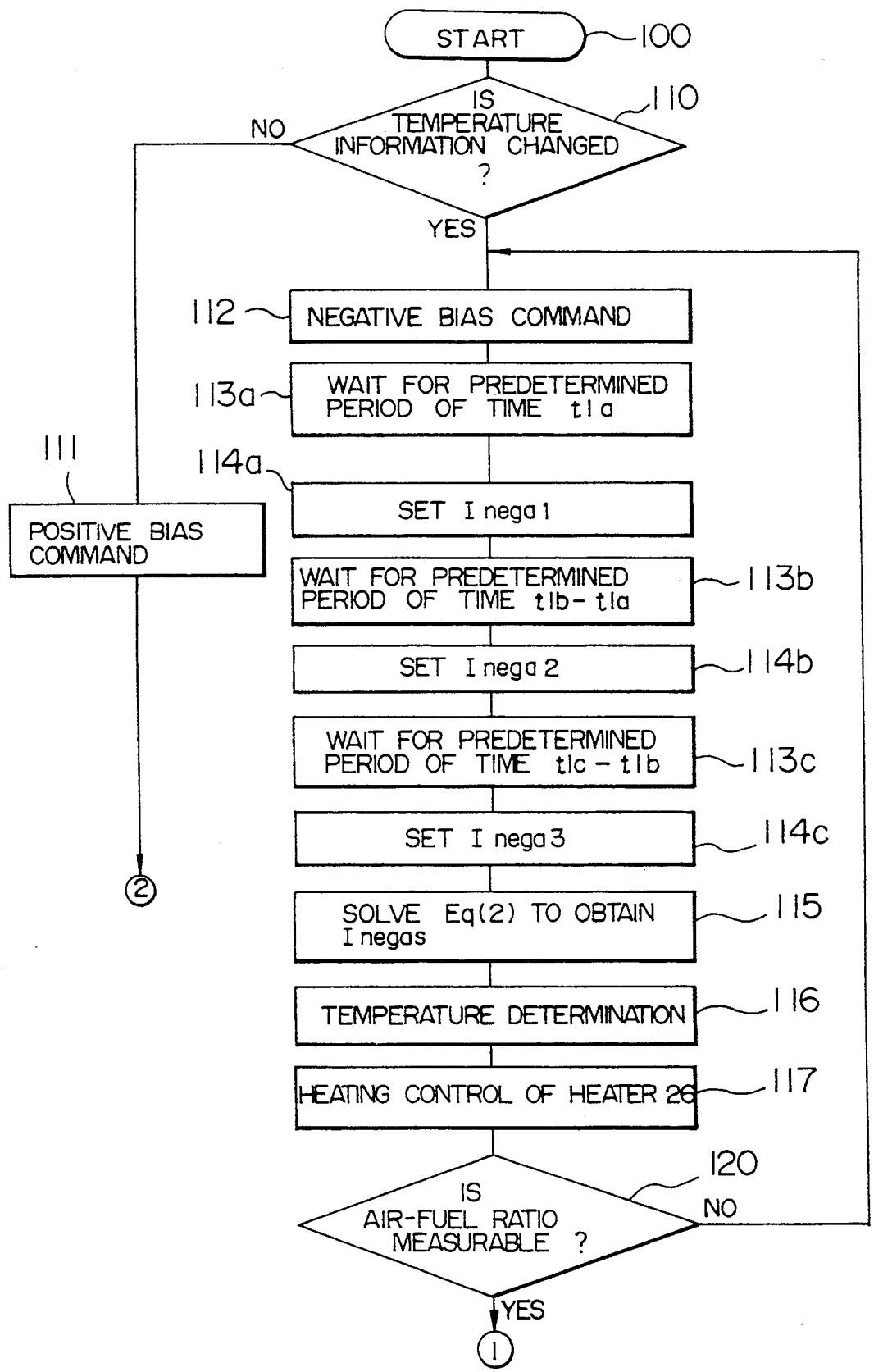

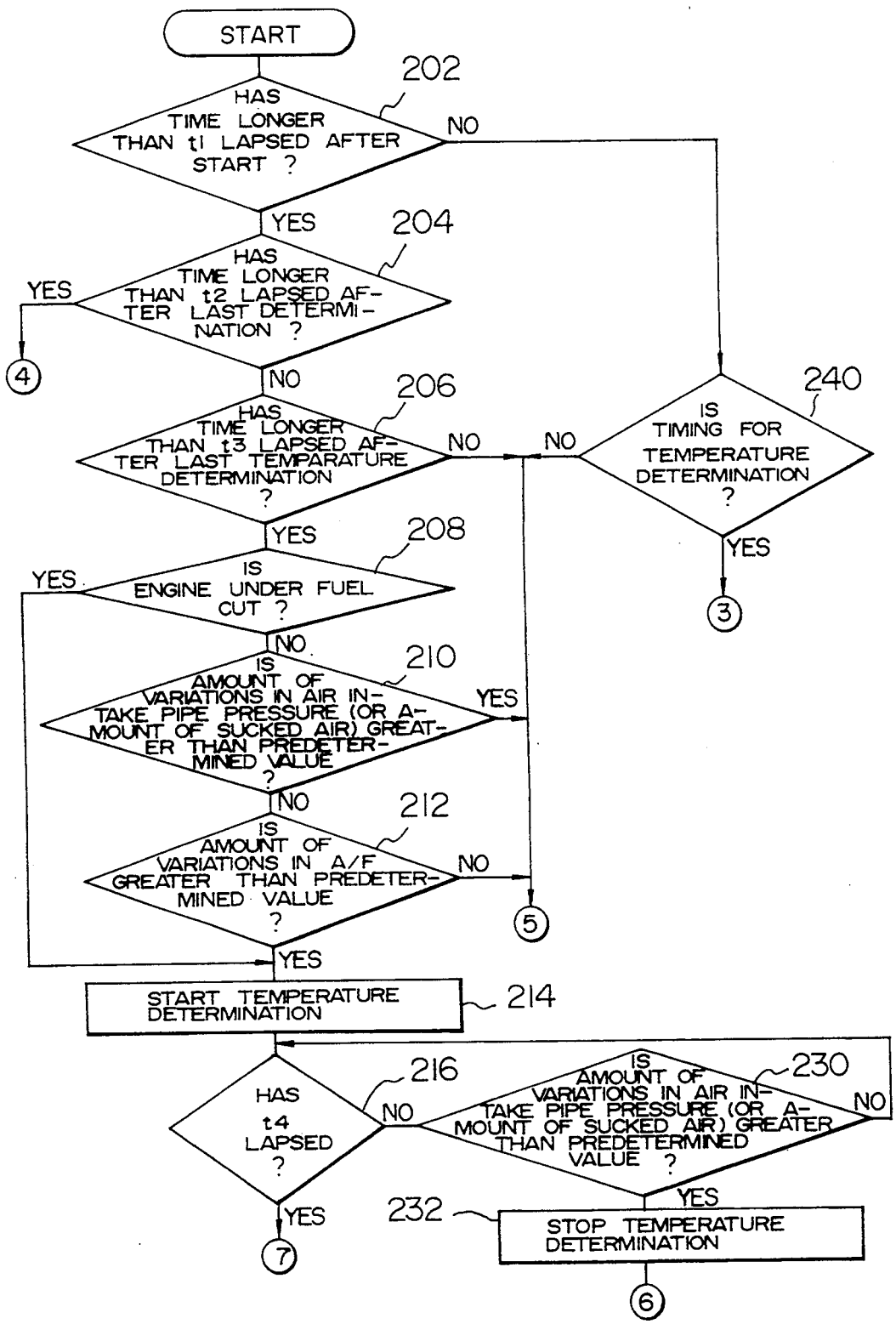

OXYGEN CONCENTRATION MEASURING DEVICE

BACKGROUND OF THE INVENTION

Field of the Invention

The present invention relates to an oxygen concentration measuring device for determining the air-fuel ratio of an air-fuel mixture before burning by measuring the oxygen concentration, etc., in exhaust gas from an internal combustion engine, and in particular to an oxygen concentration measuring device suitable for measuring oxygen concentration by using a limit current type oxygen sensor.

Description of the Related Art

Heretofore, in this type of oxygen concentration measuring devices, as indicated e.g. in JP-A-59-163556, paying attention to the fact that the internal resistance of the limit current type oxygen sensor varies depending on the temperature thereof and that a current-voltage characteristic curve specifying the temperature, i.e. the internal resistance, of the oxygen sensor passes through the origin, the oxygen sensor is positively biased in a first period by means of a positive voltage source, while it is negatively biased in a second period by means of a negative voltage source. Current flowing through the oxygen sensor is detected in the first and the second periods. The oxygen concentration is determined on the basis of the current detected in the first period, while the internal resistance of the oxygen sensor is determined on the basis of the current detected in the second period. In this way, the air-fuel ratio is reliably measured on the basis of the oxygen concentration thus detected, while controlling the temperature of the oxygen sensor at a high level of precision so as to maintain the sensor within an active region.

On the other hand, as indicated in JP-B-1-28905 and JP-B-1-25419, paying attention to the fact that the internal resistance and the temperature of the oxygen sensor correspond to each other in a one-to-one relationship, the restriction on the usable temperature region and the region where oxygen concentration can be measured is removed by detecting the internal resistance of the oxygen sensor, by calculating the voltage applied to the oxygen sensor, starting from the detection value thus obtained, and applying the voltage to the oxygen sensor on the basis of the calculation.

However, in such a construction, because the second period described previously is repeated uniformly, even in a state where the air-fuel ratio can be measured stably, the air-fuel ratio can be measured only after the second period has lapsed, which gives rise to an inconvenience that the period in which the air-fuel ratio can be measured is retarded. Further, since the second period described above is set repeatedly, independently from a temperature decrease of the oxygen sensor, the period in which the negative voltage is applied to the oxygen sensor is not always in accordance with a point of time where the temperature of the oxygen sensor begins to decrease. Consequently, if the temperature of the oxygen sensor is lowered too much before the period in which the negative voltage is applied and after the state where the air-fuel ratio can be stably measured has been once established, a long period of time is required before the air-fuel ratio can be measured stably because the response to the temperature of the oxygen sensor is slow, even if the temperature control as described above is effected by applying the negative voltage. In such a case, because the second period described above is set at a period of time required for stabilizing the internal resistance of the oxygen sensor, this causes the period in which the air-fuel ratio can be stably measured to be further retarded.

Furthermore, because the voltage applied to the oxygen sensor is continuously varied corresponding to variations in the internal resistance of the oxygen sensor, the amount of data is increased extremely. On the other hand, if data are interpolated in order to decrease the amount of data, measurement precision of the internal resistance is reduced correspondingly and, in addition, a period of time for measuring the internal resistance is increased.

SUMMARY OF THE INVENTION

Therefore, the present invention solves these problems and provides an oxygen concentration measuring device which makes it possible to shorten remarkably a period of time where the oxygen concentration cannot be measured and to decrease significantly the amount of data for determining the voltage to be applied.

In order to achieve the above object, an oxygen concentration measuring device according to the present invention comprises, as indicated in FIG. 1, for example, a limit current type oxygen sensor 6; voltage applying means 1 for applying voltage to the oxygen sensor 6; current detecting means 2 for detecting current flowing through the oxygen sensor 6 due to the voltage applied thereto; temperature measuring means 3 for measuring temperature of the oxygen sensor 6 on the basis of the current thus detected; and oxygen concentration measuring means 4 for measuring oxygen concentration on the basis of the current thus detected, when it is judged in connection with the temperature thus measured that the oxygen sensor 6 is in an almost active state; wherein the voltage applying means 1 has negative bias means 1a for negatively biasing the oxygen sensor 6. Further, one of characteristic points of the present invention resides in that a further current estimating means 5 is provided, which estimates a variation termination value of the current flowing through the oxygen sensor 6 negatively biased by the negative bias means 1a at a point of time in a variation process thereof.

Another oxygen concentration measuring device according to the present invention comprises a limit current type oxygen sensor; voltage applying means for applying voltage to the oxygen sensor; current detecting means for detecting current flowing through the oxygen sensor due to the voltage applied thereto; and internal resistance measuring means for measuring internal resistance of the oxygen sensor; wherein it may comprise further applied voltage determining means for applying a voltage determined by a predetermined region of the internal resistance and a current intensity measured by the current measuring means to the oxygen sensor, when the internal resistance is in the predetermined region.

Owing to the construction as described above of the present invention, in the oxygen concentration measuring device according to the present invention indicated in FIG. 1, when the negative bias means 1a in the voltage applying means 1 applies a voltage to the oxygen sensor 6, the current detecting means 2 detects current flowing through the oxygen sensor 6; the current estimating means 5 estimates a variation termination value of the current flowing through the oxygen sensor 6 negatively biased by the negative bias means 1a at a point of time in a variation process thereof; the temperature measuring means 3 measures the temperature of the oxygen sensor 6 on the basis of the value of the estimated current at an end of variations in the current; and the oxygen concentration measuring means 4 measures oxygen concentration on the basis of the current thus detected, when it is judged in connection with the temperature thus measured that the oxygen sensor 6 is in an almost active state.

In this way, when the temperature of the oxygen sensor 6 is measured, because the variation termination current is estimated by using the current at a period of time before the current flowing through the oxygen sensor 6 finishes to vary after having negatively biased the oxygen sensor 6 and the temperature of the oxygen sensor 6 is measured by using it, it is possible to realize rapidly the period thereafter in which the oxygen concentration can be measured.

Further, in the other oxygen concentration measuring device according to the present invention, even if the internal resistance of the oxygen sensor varies, it is possible to measure the air-fuel ratio in a large region thereof and to obtain a precise air-fuel ratio because the internal resistance at that time is measured and a voltage for which current is within a limit current region corresponding thereto is applied thereto. Further, when the internal resistance of the sensor is within a predetermined region, because the applied voltage is varied only stepwise for the internal resistance varying continuously without interruption by determining the voltage applied to the oxygen sensor by using the predetermined region and the intensity of the detected current, compared with a method, by which the applied voltage is varied continuously as disclosed in JP-B-1-28905, the number of applied voltages can be reduced remarkably and together therewith the amount of data for determining the applied voltage can be significantly decreased. In addition, a short period of time is sufficient from a detection of the internal resistance of the oxygen sensor to the succeeding detection of the air fuel ratio owing to detection of the current intensity before it arrives at a convergence value after having applied the negative bias thereto and the time, in which the detection of the air fuel ratio is impossible, can be remarkably shortened.

BRIEF DESCRIPTION OF THE DRAWINGS

FIG. 7 is a flow chart showing the operation of the microcomputer in a first modified example of the first embodiment;

FIG. 8 is a flow chart showing the operation of the microcomputer in a second modified example of the first embodiment;

DESCRIPTION OF THE PREFERRED EMBODIMENTS

Figure 1:
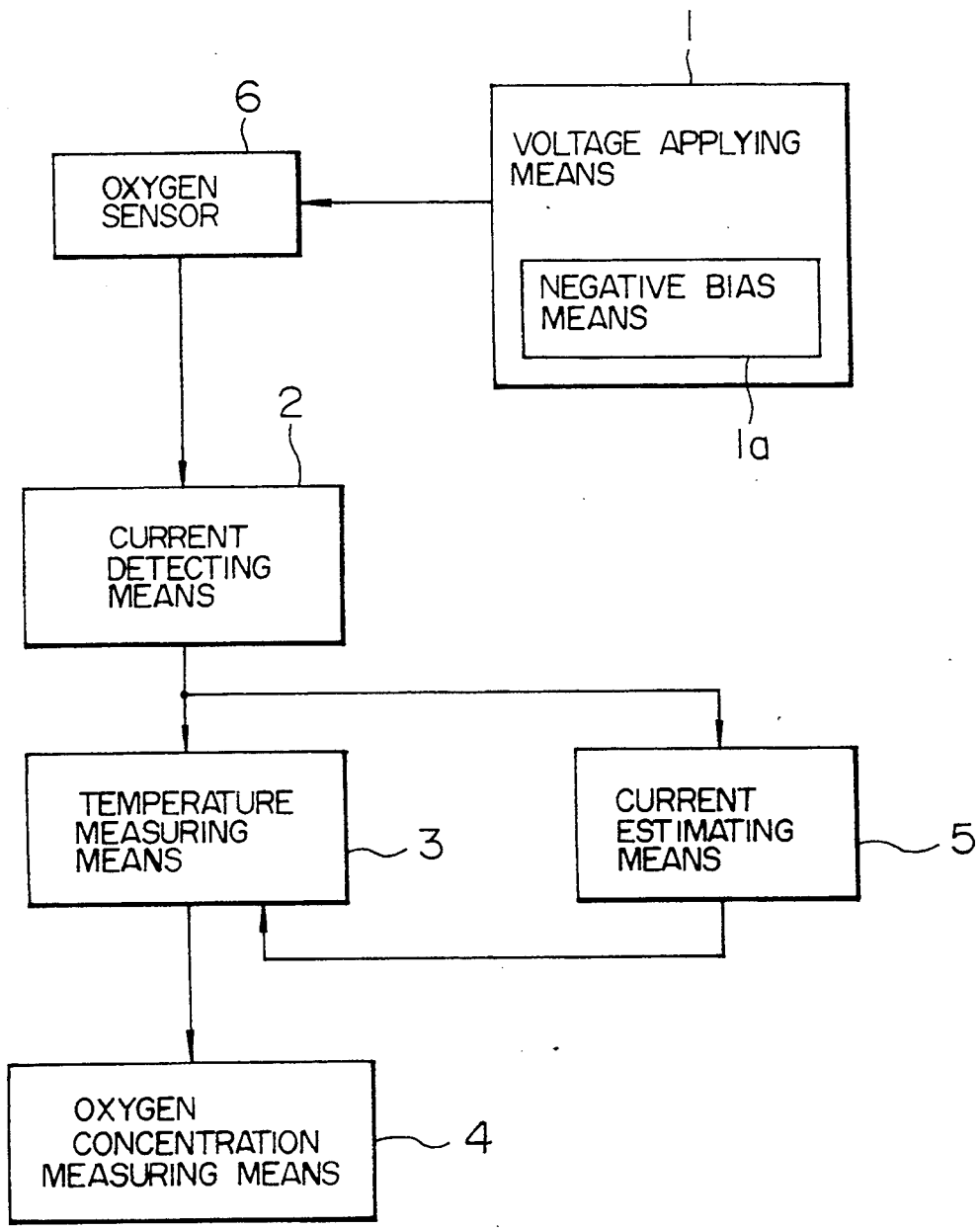
FIG. 1 is a block diagram showing the principle of the oxygen concentration measuring device according to the present invention.
Figure 2:
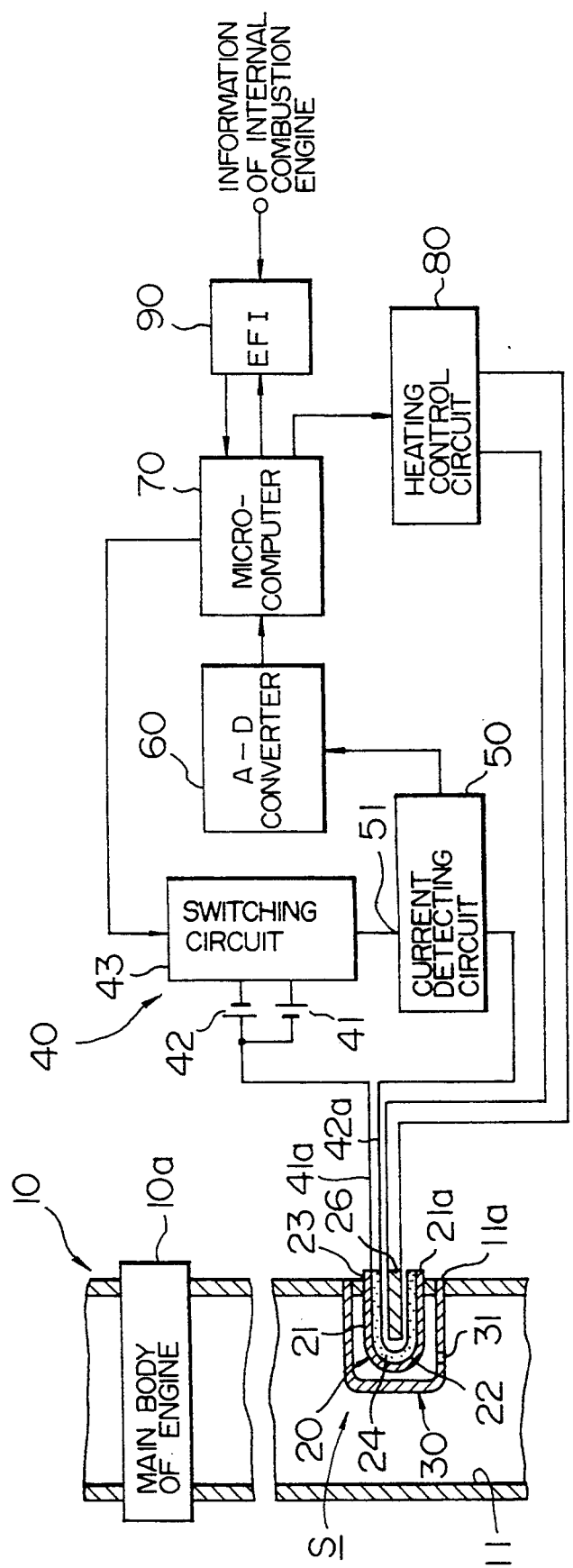
FIG. 2 is a block circuit diagram showing a first embodiment of the present invention.

Hereinbelow a first embodiment of the present invention will be explained, referring to the drawings. FIG. 2 shows an example of the oxygen concentration measuring device according to the present invention applied to an internal combustion engine 10. The oxygen concentration measuring device is provided with a limit current type oxygen sensor S. This oxygen sensor S is mounted in an exhaust pipe 11 extending from the main body 10a of the internal combustion engine 10. The oxygen sensor S comprises a sensor main body 20 and a cover 30 having a U shaped cross-section. The sensor main body 20, the bottom portion of which is inserted in a mounting hole portion 11a formed in a part of the wall of the exhaust pipe 11, extends towards the interior of the exhaust pipe 11.

Figure 3A:
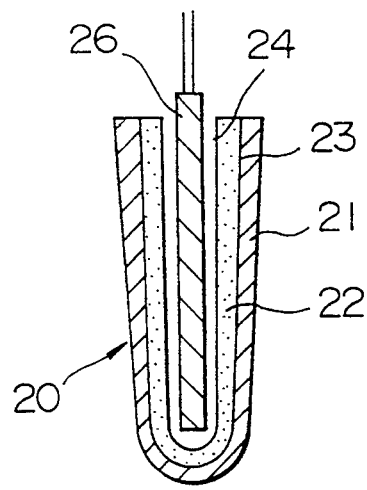
FIG. 3A is an enlarged cross-sectional view of the main body of the oxygen sensor indicated in FIG. 2.

The sensor main body 20 includes a diffusion resisting layer 21 having a cup shaped cross-section. This diffusion resisting layer 21 is inserted in the mounting hole portion 11a of the exhaust pipe 11 at the opening end portion 21a thereof. The diffusion resisting layer 21 is formed by plasma melting ejection method, etc. with $ZrO_2$, etc. Further, as indicated in FIG. 3A in detail, the sensor main body 20 includes a solid electrolyte layer 22. This solid electrolyte layer 22 is made of oxygen ion conductive oxide sintered body formed in a cup shape in cross section, deposited uniformly on the inner surface of the diffusion resisting layer 21 through an exhaust gas side electrode layer 23 cup-shaped in cross section. An atmosphere side electrode layer 24 cup-shaped in cross section is secured uniformly on the inner surface of this solid electrolyte layer 22. In such a case both the exhaust gas side electrode layer 23 and the atmosphere side electrode layer 24 are made of noble metal having a high catalytic activity such as platinum formed so as to be satisfactorily porous by chemical plating, etc. The area and the thickness of the exhaust gas side electrode layer 23 are about 10 to 100 $mm^2$ and 0.5 to 2.0 $\mu m$, respectively. On the other side the area and the thickness of the atmosphere side electrode layer 24 are greater than 10 $mm^2$ and about 0.5 to 2.0 $\mu m$, respectively.

The sensor main body 20 thus constructed generates a concentration electromotive force at the theoretical air fuel ratio point and produces a limit current corresponding to the oxygen concentration in the lean domain with respect to the theoretical air fuel ratio point. In such a case, the limit current corresponding to the oxygen concentration is determined by the area of the exhaust gas side electrode layer 23 as well as the thickness, the porocity and the average pore diameter of the diffusion resisting layer 21. The sensor main body 20 can detect the oxygen concentration by using linear characteristics thereof. However since a temperature higher than about 650° C. is required for activating this sensor main body 20 and the same sensor main body 20 has a narrow activation temperature region, active region thereof cannot be controlled by heating only by using exhaust gas from the internal combustion engine. For this reason heating control of a heater described later is used. In the rich side domain with respect to the theoretical air-fuel ratio, concentration of carbon monoxide (CO), which is not burned gas, varies approximately linearly with respect to the air-fuel ratio and a limit current corresponding thereto is produced.

Now the voltage-current characteristics of the sensor main body 20 using the temperature of the same sensor main body 20 as a parameter will be explained. These voltage-current characteristics indicate that the relation between the current flowing in the solid electrolyte layer 22 of the sensor main body 20, which is proportional to the oxygen concentration (air-fuel ratio) detected by the oxygen sensor S and the voltage applied to the same solid electrolyte layer 22 is linear and that, when the sensor main body 20 is in an active state at a temperature T=T1, it is in a stable state represented by a characteristic graph L1 as indicated by full lines in FIG. 3B. In such a case, straight line portions of the characteristic graph L1, which are parallel to the voltage axis V, specify limit currents of the sensor main body 20. Increase or decrease in the limit current corresponds to increase or decrease in the air-fuel ratio (i.e. lean or rich). When the temperature T of the sensor main body 20 is at T2, which is lower than T1, voltage-current characteristics at that time are indicated by a characteristic graph L2 as indicated by broken lines in FIG. 3B. In such a case, straight line portions of the characteristic graph L2, which are parallel to the voltage axis V, specify limit currents of the sensor main body 20 at T=T2. These limit currents are almost in accordance with the limit currents indicated by the characteristic graph L1.

Figure 3B:
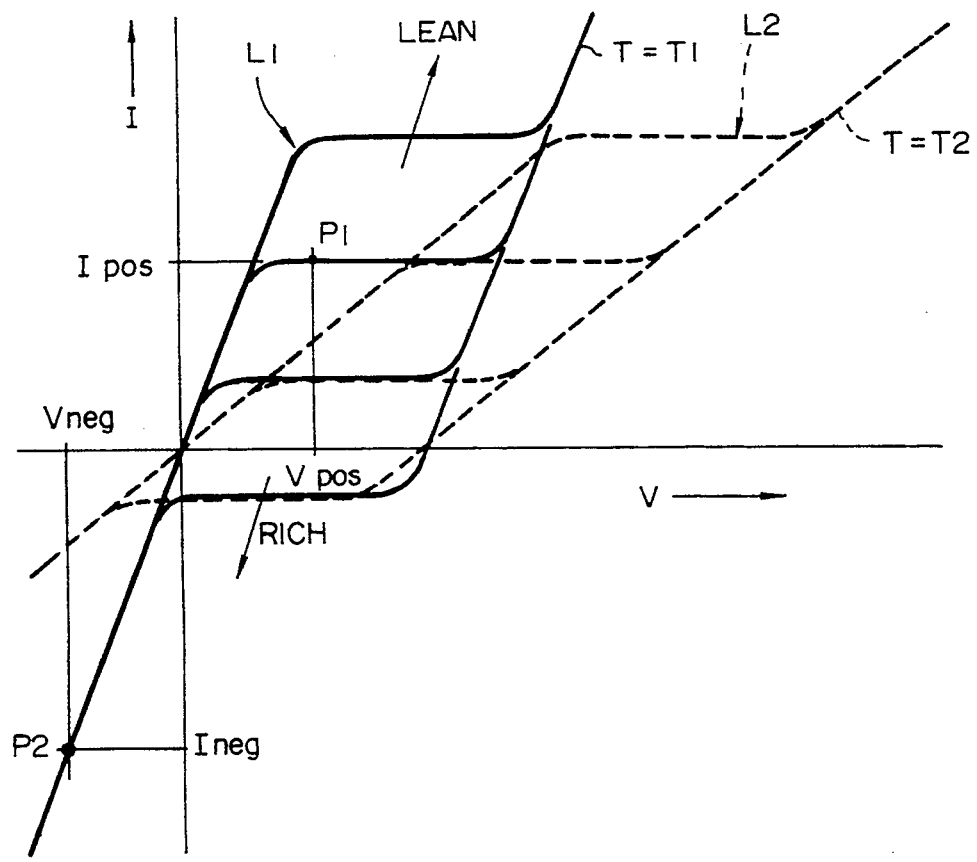
FIG. 3 is a graph indicating limit current-voltage characteristics for the oxygen sensor, using temperature as a parameter.

In the characteristic graph L1, when a positive voltage Vpos is applied to the solid electrolyte layer 22 in the sensor main body 20, current flowing through the sensor main body 20 is the limit current Ipos at that time (refer to point P1 in FIG. 3B). On the contrary, when a negative voltage Vneg is applied to the solid electrolyte layer 22 in the sensor main body 20, current flowing through the sensor main body 20 is a negative current Ineg specified by a point P2, which is independent from the oxygen concentration and proportional only to the temperature. Therefore it is possible to keep the internal resistance of the sensor main body 20 constant to maintain the same sensor main body 20 in an active state by heating control of a heater 26, using the current Ineg at that time.

The sensor main body 20 includes the heater 26, which is accommodated in the atmosphere side electrode layer 24 and heats the atmosphere side electrode layer 24, the solid electrolyte layer 22, the exhaust gas side electrode layer 23 and the diffusion resisting layer 21 by heating energy thereof. In such a case, the heater 26 has a heating capacity sufficient for activating the sensor main body 20. As indicated in FIG. 2, a cover 30 covers the sensor main body 20 and the opening portion thereof is inserted into a part of the peripheral wall of the exhaust pipe 11. A small hole 31 is formed in a part of the peripheral wall of the cover for communicating the exterior of the cover 30 with the interior thereof. In this way, the cover 30 secures temperature keeping of the sensor main body 20 while preventing direct contact of the sensor main body 20 with exhaust gas.

Further, as indicated in FIG. 2, the oxygen concentration measuring device is provided with a bias control circuit 40. This bias control circuit 40 consists of a positive biasing DC power source 41, a negative biasing DC power source 42 and a switching circuit 43. The DC power source 41 is connected with an end of the exhaust gas side electrode layer 23 through a wire 41a by the negative side electrode thereof, while the DC power source 42 is connected with another end of the exhaust gas side electrode layer 23 through the wire 41a by the positive side electrode thereof. The switching circuit 43 is constructed so as to connect only the positive side electrode of the DC power source 41 with an input terminal 51 of a current detecting circuit 50 in a first switching state and on the contrary only the negative side electrode of the DC power source 42 with the input terminal 51 of the current detecting circuit 50 in a second switching state. The switching circuit 43 is connected with the atmosphere side electrode layer 24 from the input terminal 51 through the current detecting circuit 50 and further through another wire 42a. Consequently, when the switching circuit 43 is in the first switching state, the DC power source 41 biases positively the solid electrolyte layer 22 and makes current flow through the solid electrolyte layer 22 in a positive direction. On the contrary, when the switching circuit 43 is in the second switching state, the DC power source 42 biases negatively the solid electrolyte layer 22 and makes current flow through the solid electrolyte layer 22 in a negative direction. In such a case terminal voltages of the DC power sources 41 and 42 correspond to the applied voltages Vpos and Vneg, respectively.

The current detecting circuit 50 detects current flowing from the atmosphere side electrode layer 24 in the sensor main body 20 to the switching circuit 43 or current flowing in a reverse direction, i.e. current flowing through the solid electrolyte layer 22 and outputs it to an A-D converter 60. This A-D converter 60 converts the current thus detected into a digital value, which is outputted to the microcomputer 70. The microcomputer 70 executes a computer program according to the flow chart indicated in FIG. 4 in collaboration with the A-D converter 60 and in this execution it effects calculation processing necessary for controlling a heating control circuit 80 and an electronic fuel injection control device (hereinbelow called EFI) 90. The computer program described above is previously stored in an ROM of the microcomputer 70. Further the heating control circuit 80 effects heating control of the heater 26 under the control by the microcomputer 70. In addition, the EFI 90 effects fuel injection control according to information of internal combustion engine such as amount of exhaust gas, number of rotations, flow rate of sucked air, air intake pipe negative pressure, temperature of cooling water, etc. of the internal combustion engine 10.

Figure 4:
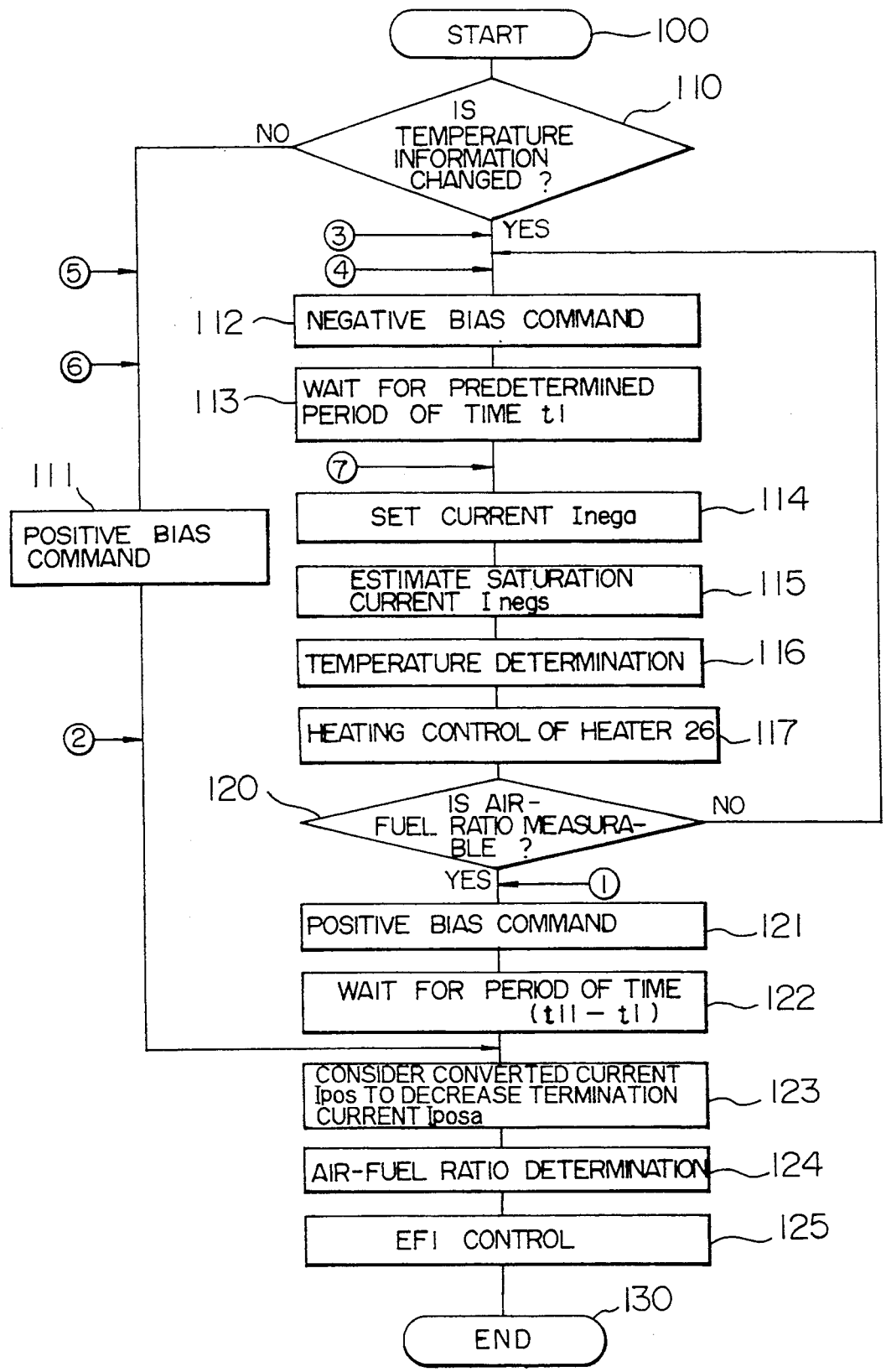
FIG. 4 is a flow chart showing the operation of the microcomputer indicated in FIG. 2.

In the first embodiment thus constructed, it is supposed that the microcomputer 70 executes the computer program repeatedly after having started execution of the computer program at Step 100 according to the flow chart indicated in FIG. 4. Further, at the present stage, it is supposed that the oxygen sensor is stable in the active state. Unless the information of internal combustion engine is changed suddenly, it is judged that temperature information on the sensor main body 20 is unnecessary and judgment "NO" is repeatedly issued at Step 110.

In such a state, the microcomputer 70 makes the computer program proceed to Step 111 and Step 123 and the followings indicated in FIG. 4 and outputs a positive bias command, which is necessary for applying a positive voltage Vpos to the sensor main body 20, to the switching circuit 43 in the bias control circuit 40. Then the switching circuit 43 is changed to be in the first switching state, responding to the positive bias command, and connects the positive side electrode of the DC power source 41 with the input terminal 51 of the current detecting circuit 50. In this way, the current Ipos from the DC power source 41 flows through the current detection circuit 50, the wire 42a, the atmosphere side electrode 24, the solid electrolyte layer 22, the exhaust gas side electrode 23 and the wire 41a as a limit current.

Then the current detecting circuit 50 detects the inflow current Ipos and the A - D converter converts the detected inflow current Ipos into a digital value to output it to the microcomputer 70. The current Ipos thus converted is inputted to the microcomputer 70 at Step 123, which sets a decrease termination current Iposa and determines the oxygen concentration, i.e. air-fuel ratio, corresponding to the decrease termination current Iposa, i.e. limit current, on the basis of oxygen concentration-limit current data indicated in FIG. 5C at Step 124. The oxygen concentration-limit current data are stored previously in an ROM of the microcomputer 70 as data specifying the linear relationship between the oxygen concentration, i.e. air-fuel ratio, in the exhaust gas and the limit current of the sensor main body 20 at a temperature T=T1. When the air-fuel ratio is determined in this way, the microcomputer 70 effects calculating processing necessary for fuel injection control by the EFI 90 at Step 125, taking the determined air-fuel ratio into account. In this way, the EFI 90 effects the fuel injection control for the internal combustion engine 10 on the basis of the calculating processing.

Figure 5A:
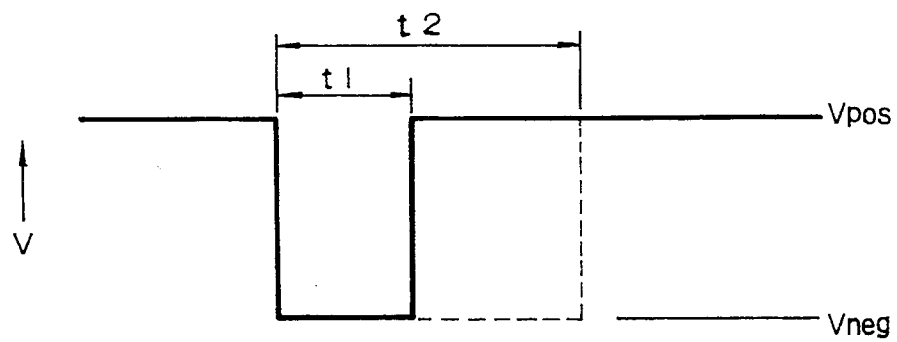
FIG. 5A is a time chart showing variations in the voltage applied to the sensor main body at negative and positive biases.

In such a state, when the amount of exhaust gas, the number of rotations., or the intake air flow rate for the internal combustion engine 10 coming from the EFI 90 is changed suddenly, it is judged that temperature information has been changed and the microcomputer 70 judges "YES" at Step 110 to output a negative bias command, which is necessary for applying a negative applied voltage Vneg to the sensor main body 20, to the switching circuit 43 in the bias control circuit 40 at Step 112 (refer to FIG. 5A). Then the switching circuit 43 is changed to be in the second switching state, responding to the negative bias command, and connects the negative side electrode of the DC power source 42 with the input terminal 51 of the current detecting circuit 50. In this way, the current Ineg from the DC power source 42 (refer to full lines indicated in FIG. 5B) begins to flow through the wire 41a, the exhaust gas side electrode 23 of the sensor main body 20, the solid electrolyte layer 22, the atmosphere side electrode 24, the wire 42a and the current detection circuit 50.

After the calculation processing at Step 112 as described above, the microcomputer waits for a predetermined period of time t1 at Step 113. In such a case, the predetermined period of time t1 is determined as follows. The current Ineg increases exponentially after the application of the negative bias to the sensor main body 20, as indicated by full and broken lines in FIG. 5B. Therefore, if the current Ineg is detected, waiting until this current Ineg is saturated, as by prior art techniques, the time of succeeding determination of the air-fuel ratio is retarded. For this reason, a value Inega at a point of time in increasing process of the current Ineg is used without waiting for saturation of the current Ineg to estimate the saturation current Inegs of the current Ineg. It can be understood that the time of determining the air-fuel ratio is advanced. Therefore, the predetermined period of time t1 is selected so as to be a reasonable period of time after the application of the negative bias to the sensor main body 20 till a point of time where variation tendency of the current Ineg is maintained relatively high and stored previously in the ROM of the microcomputer 70.

Then, when the wait at Step 113 is terminated, the microcomputer 70 considers the converted current Ineg coming from the A-D converter 60 to be the current Inega at Step 114 and estimates the saturation current Inegs on the basis of a transient phenomenon equation representing the relation between the current Ineg and the applied voltage Vneg at Step 115, corresponding to the same current Inega. The transient phenomenon equation described above is constructed by using conditions at the negative bias period of the sensor main body 20 as initial conditions and stored in the ROM of the microcomputer 70. Thereafter the microcomputer 70 determines the temperature of the sensor main body 20 on the basis of estimated saturation current-temperature characteristic data at Step 116, corresponding to the estimated saturation current Inegs. The estimated saturation current-temperature characteristic data described above are stored previously in the ROM of the microcomputer 70 in the form of data representing a directly proportional relationship between the estimated saturation current |Inegs| and the temperature of the sensor main body.

When the temperature of the sensor main body 20 is determined in this way, the microcomputer 70 effects calculating processing at Step 117 for controlling heating of the heater 26 so as to increase the temperature determined at Step 116 to a temperature T1 (refer to characteristic graph L1) and to maintain it at that temperature. For this purpose, a heating control circuit 80 controls heating of the heater 26 on the basis of the heating control calculating processing by the microcomputer 70. In this way, even if the temperature of the sensor main body 20 is lowered temporarily, it returns rapidly to the temperature T1.

For this purpose, the microcomputer 70 judges "YES" at Step 120 under judgment that the device is in the state where the air fuel ratio can be stably measured and makes the computer program proceed to Step 121 and the followings. Thereafter the microcomputer 70 issues a positive bias command, which is necessary for applying a positive voltage Vpos to the sensor main body 20, to the bias control circuit 40 at Step 121. Then the bias control circuit 40 applies the voltage Vpos coming from the DC power source 41 to the sensor main body in the same way as that described previously. This means that application of the voltage Vpos to the sensor main body 20 is effected directly after lapse of the predetermined period t1 stated previously. In this way, the current Ipos from the DC power source 41 begins to flow directly after the lapse of the predetermined period t1 through the wire 41a, the exhaust gas side electrode 23, the solid electrolyte layer 22, the atmosphere side electrode 24, the wire 42a and the current detecting circuit 50 as the limit current. In other words, as indicated in FIG. 5B, the current Ineg, which is flowed through the sensor main body 20, is inverted and rises directly after the lapse of the predetermined period of time t1, as indicated by a full line, to become the current Ipos and thereafter begins to decrease exponentially.

Further, when the calculating processing at Step 121 is terminated as described above, the microcomputer 70 waits for a predetermined time (t11-t1) at the succeeding Step 122 (refer to FIGS. 5A and 5B). t11 represents a period of time from the point of time where the current Ineg begins to flow as described above to the point of time where the current Ipos, which has begun to flow directly after the lapse of the predetermined period of time t1, finishes to decrease exponentially. In such a case, the predetermined period of time (t11 - t1) is determined on the basis as described below.

Figure 5B:
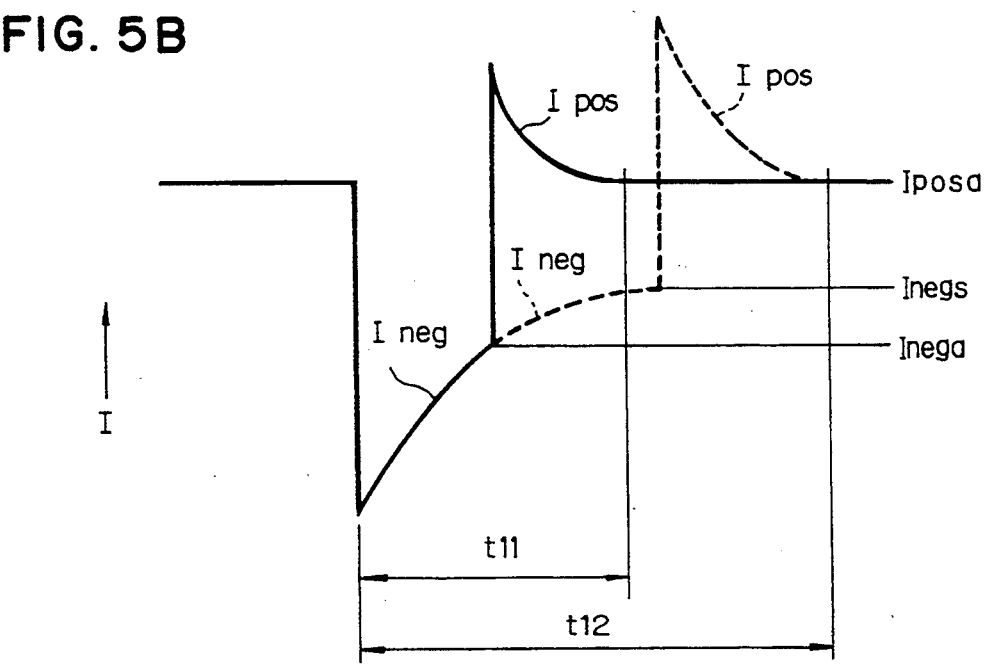
FIG. 5B is a time chart showing waveform of current flowing through the same sensor main body.

At first, a case where the current Ineg varies exponentially as indicated by the full line in FIG. 5B and the voltage Vpos is applied to the sensor main body 20 at the point of time, where it is saturated, as indicated by the broken line in the figure (refer to the broken line in FIG. 5A), to positively bias the sensor main body 20, similarly to the prior art techniques, is compared with a case where the voltage Vpos is applied to the sensor main body 20 directly after the lapse of the predetermined period of time t1 (refer to the full line in FIG. 5A), as defined according to the present invention, where t2 represents a period of time necessary for saturation of the current Ineg in the prior art case, as indicated in FIG. 5A.

In such a case, durations until the current Ipos due to the application of the voltage Vpos finishes to decrease, are approximately equal for the prior art case and the case of this first embodiment, based on a physical phenomenon proper to the sensor main body 20. Consequently, denoting the period of time until the current Ipos finishes to decrease exponentially in the prior art case by t22, as indicated in FIG. 5B, the point of time where the current Ipos begins to flow in the case of this first embodiment (refer to the full lines indicated in FIGS. 5A and 5B) is earlier than the point of time where the current Ipos begins to flow in the prior art case (refer to the broken lines indicated in FIGS. 5A and 5B) by a period of time (t2 - t1) and corresponding thereto, the point of time where the current Ipos finishes to decrease in the case of this first embodiment is earlier than the point of time where the current Ipos finishes to decrease in the prior art case. Further, the point of time where the current Ipos begins to flow in the case of this first embodiment corresponds to a point of time in the middle course of the rise of the current Ineg, while the point of time where the current Ipos begins to flow in the prior art case corresponds to the point of time where the current Ineg finishes rising. In this way, the concentration of oxygen accumulated in the neighborhood of the exhaust gas side electrode 23 during the period of time where the sensor is negatively biased is reduced, compared with that obtained by the prior art techniques. For this reason, the rising peak level of the current Ipos is lowered. Further, the time constant at the decrease of the current Ipos becomes smaller and thus the current Ipos decreases more rapidly. The degree of these two effects depends on the amount of electric charge conducted during the period of time, where the sensor is negatively biased. That is, with shorter t1 to decrease the amount of electric charge the two terms stated above become smaller and t11 is further shortened. Consequently, denoting the period of time from the point of time where the current Ineg begins to flow to the point of time where the current Ipos finishes to decrease in the prior art case by t22, as indicated in FIG. 5B, the latter in the present embodiment is earlier than that in the prior art case by (t22 - t11). Therefore the predetermined period of time is set at (t11 - t1), which is stored previously in the ROM of the microcomputer 70.

When the wait at Step 122 is terminated, the converted current Ipos coming from the A-D converter 60 directly after the lapse of the predetermined period of time t11 is inputted to the microcomputer at Step 123 and set therein as the decrease termination current Iposa. At Step 124 the oxygen concentration, i.e. the air-fuel ratio, is determined, corresponding to the decrease termination current Iposa, i.e. the limit current, on the basis of the oxygen concentration-limit current data described previously (refer to FIG. 5C). When the air-fuel ratio is determined in this way, the microcomputer 70 executes the calculating processing necessary for fuel injection control by the EFI 90, taking the air-fuel ratio thus obtained into account, at Step 125. In this way the EFI 90 effects fuel injection control for the internal combustion engine 10 on the basis of the calculating processing.

As explained above, since the saturation current Inegs is estimated, starting from the current Inega at a point of time (after the lapse of the predetermined period of time t1) before the current Ineg flowing through the sensor main body 20 finishes to rise, after the sensor main body 20 has been negatively biased by the applied voltage Vneg, when the temperature of the sensor main body 20 should be determined, and the temperature of the sensor main body 20 is determined in this way, it is possible to realize rapidly a period of time succeeding it, in which the air-fuel ratio can be measured. In such a case, since the temperature of the sensor main body 20 is determined only when it is judged at Step 110 that there are variations in information on the temperature of the sensor main body 20, it is possible to realize earlier the period of time, in which the air-fuel ratio can be measured, than by the prior art techniques, by which the temperature is determined periodically.

Further, since the temperature of the sensor main body 20 is determined only when it is judged at Step 110 that there are variations in information on the temperature of the sensor main body 20, variation time in the temperature information is substantially in accordance with temperature determination time. For this reason, since the heater 26 is controlled in heating by the heating control circuit 80 early before the temperature of the sensor main body 20 is lowered improperly, it is possible to make the temperature of the sensor main body 20 return immediately to the temperature T1 (refer to FIG. 3B). Consequently heating control time for the heater 26 can be further shortened, while preventing beforehand improper temperature lowering of the sensor main body 20, which is apt to take place in the case where temperature determination is effected periodically as by the prior art techniques. As the result, it is possible to realize rapidly the period of time succeeding it in which the air fuel ratio can be measured.

Further, since the air-fuel ratio is determined by using the current Ipos at the moment, where the sensor main body 20 is positively biased by the applied voltage Vpos directly after the lapse of the predetermined period of time t1 and the current Ipos flowing through the sensor main body 20 finishes to decrease due to this positive bias, i.e. after the lapse of the predetermined period of time (t11 - t1), it is possible to determine the air-fuel ratio earlier than by the prior art techniques. In such a case, since the rising peak level of the current Ipos in the case of the first embodiment is maintained relatively low with respect to the rising peak level of the current Ipos in the prior art case and the current Ipos in the case of the present invention decreases more rapidly than the current Ipos in the prior art case, as described above, it is possible to determine more rapidly the air-fuel ratio. The current Iposa, by which the current Ipos finishes to decrease, may be estimated in the course of decrease of the current Ipos to know earlier variations in the air-fuel ratio.

Furthermore, although the sensor main body 20 is positively biased by the applied voltage Vpos directly after the lapse of the predetermined period of time t1 in the first embodiment, not restricted thereto, it may be executed by biasing positively the sensor main body 20 by the applied voltage Vpos before the lapse of the predetermined period of time t11.

Now a first modified example of the first embodiment described above will be explained. In the first embodiment described above, when the saturation current Inegs of the current Ineg is estimated, the current Inega is determined by measuring it only once at a certain point of time in the increase process of the current Ineg. Contrarily thereto, the characteristic point of this first modified example is that the saturation current Inegs of the current Ineg is estimated by measuring the current Inega at three points of time in the increase process of the current Ineg. In this way it is possible to estimate more precisely the saturation current Inegs.

Figure 6A:
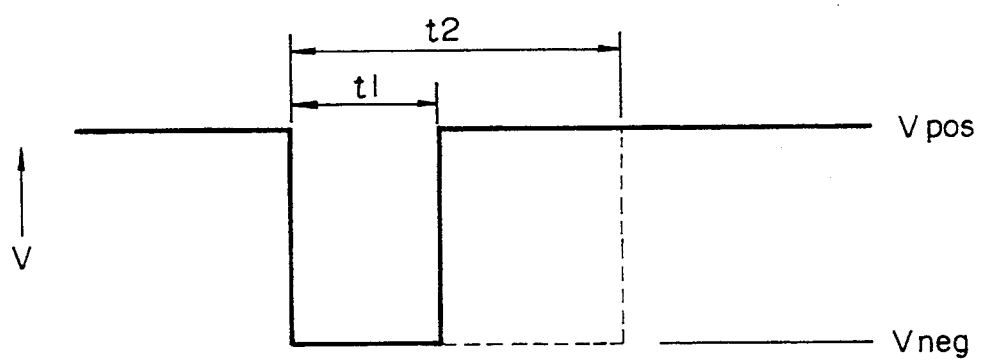
FIG. 6A is another time chart showing variations in the voltage applied to the sensor main body at negative and positive biases.
Figure 6B:
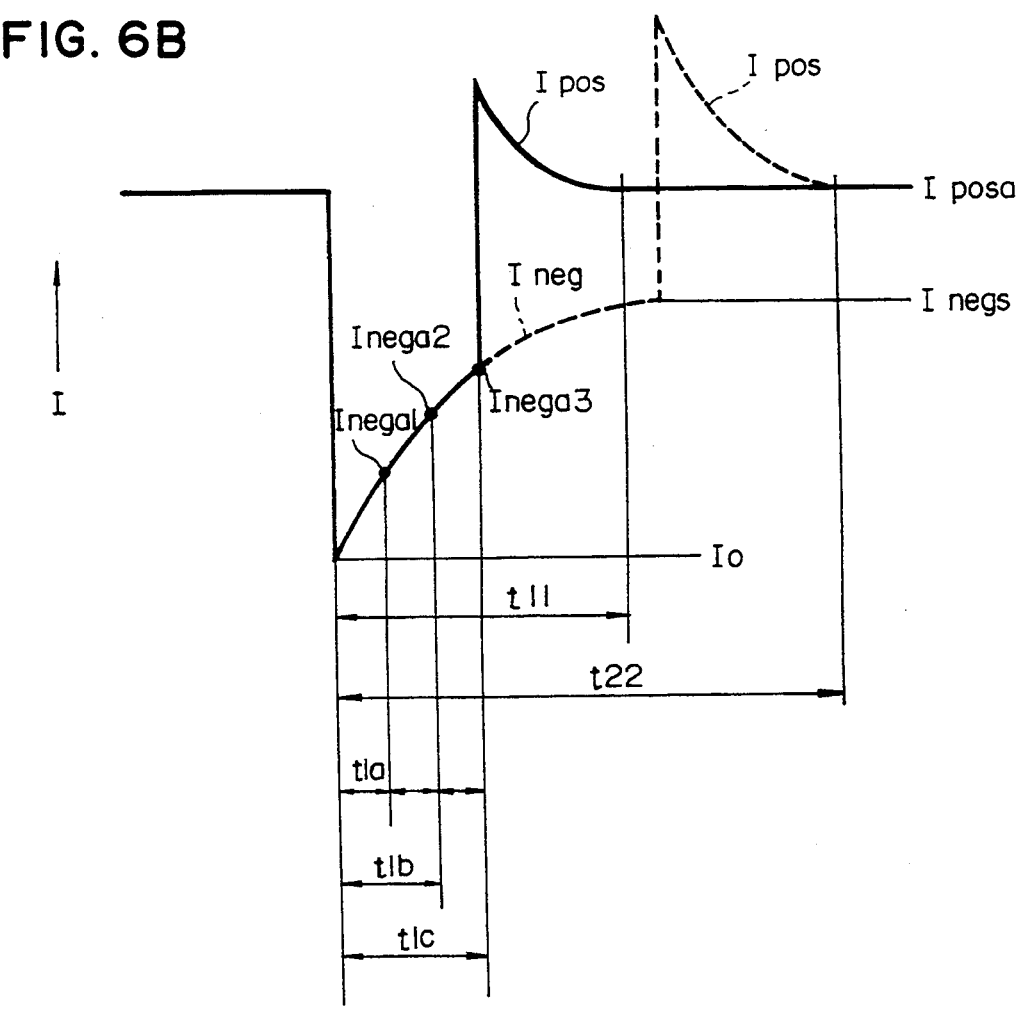
FIG. 6B is another time chart showing waveform of current flowing through the same sensor main body.

FIGS. 6A and 6B are diagrams indicating the voltage V applied to the sensor main body 20 and the current I flowing through the sensor 20 at that time, similarly to FIGS. 5A and 5B. In FIGS. 6A and 6B, the current Ineg flowing when the applied voltage V is switched from Vpos to Vneg varies exponentially, as indicated by the following Eq. (1), where the peak current intensity is represented by $I_0$, the saturation current intensity (converged current intensity) by Inegs, and the time constant by T;

$$Ineg = Inegs + (I_0 - Inegs)e^{-t/T} \tag{1}$$

Here, in the case where the peak current intensity $I_0$, the saturation current intensity (converged current intensity) Inegs and the time constant T are unknown, it is necessary to measure the current intensity at 3 points Inega1, Inega2 and Inega3 on the Ineg curve, in order to obtain Inegs. By solving simultaneous equations given by the following Eq. (2) using current intensities Inega1, Inega2 and Inega3 thus detected at the 3 points, a solution thereof, i.e. Inegs, is obtained;

$$\left. \begin{array}{l} Inega1 = Inegs + (I_0 - Inegs)e^{-t1a/T} \\ Inega2 = Inegs + (I_0 - Inegs)e^{-t1b/T} \\ Inega3 = Inegs + (I_0 - Inegs)e^{-t1c/T} \end{array} \right\} \tag{2}$$

Here Inega1, Inega2 and Inega3 are values of the current Ineg after three times t1a, t1b and t1c, respectively, measured from the point of time where the applied voltage V is changed from Vpos to Vneg. For example, in order to simplify calculation, putting t1a=0 and t1b=t1c−t1b, substituting these values for t1a and t1b in Eq. (2) to obtain Inegs, Inegs is given by Eq. (3);

$$Inegas = (Inega2^2 - Inega3.Inega1)/(2Inega2 - Inega3 - Inega1) \tag{3}$$

Now the operation of this first modified example will be explained, referring to the flow chart indicated in FIG. 7. A difference of this first modified example from the first embodiment described previously consists in that the steps from Step 113 to Step 115 in FIG. 4 are replaced by steps from Step 113a to Step 115 in FIG. 7. Therefore the steps from Step 100 to Step 112 are identical to those described for the first embodiment and explanation thereof will be omitted.

After the calculating processing at Step 112, the microcomputer 70 waits for the predetermined period of time t1a at Step 113a. When the wait at Step 113a is terminated, the microcomputer 70 detects the current intensity at Step 114a and considers the converted current Ineg coming from the A-D converter 60 as the current Ineg1. Thereafter, the microcomputer 70 waits for the predetermined period of time t1b at Step 113b.

When the wait at Step 113b is terminated, the microcomputer 70 detects the current intensity at Step 114b and considers the converted current Ineg coming from the A-D converter 60 as the current Ineg2. Then the microcomputer 70 waits for the predetermined period of time t1c at Step 113c.

When the wait at Step 113c is terminated, the microcomputer 70 detects the current intensity at Step 114c and considers the converted current Ineg coming from the A-D converter 60 as the current Ineg3. Thereafter the microcomputer 70 calculates the saturation current Inegs on the basis of the simultaneous equations given by Eq. (2) at Step 115. In such a case, the simultaneous equations given by Eq. (2) are constructed using conditions at the period of time where the sensor main body 20 is negatively biased as initial conditions and stored previously in the ROM of the microcomputer 70. Thereafter, the microcomputer 70 determines the temperature of the sensor main body 20 on the basis of the saturation current-temperature characteristic data at Step 116, corresponding to the saturation current Inegs obtained at Step 115. Since the succeeding steps from Step 117 to Step 130 are identical to those described in the first embodiment, explanation thereof is omitted.

As explained above, the characteristic point of the first modified example consists in that the current Inega is measured at three points of time in the increase process of the current Ineg to estimate the saturation current Inegs of the current Ineg. Thus, it is possible to estimate more precisely the saturation current Inegs.

Next a second modified example of the first embodiment. Although, in the first embodiment described previously, explanation has been made, supposing that the oxygen sensor S is in an active state and stable, the oxygen sensor S is yet in an inactive state and in an unstable state directly after start of the engine. This second modified example relates to a processing after the start of the engine until the oxygen sensor is in the active state and the unstable state is removed. Therefore, after the oxygen sensor has entered the active state and in the stable state, it executes operations similar to those described previously for the first embodiment. FIG. 8 is a flow chart for explaining the operations of the second modified example, which will be explained below according to this flow chart.

Figure 9:
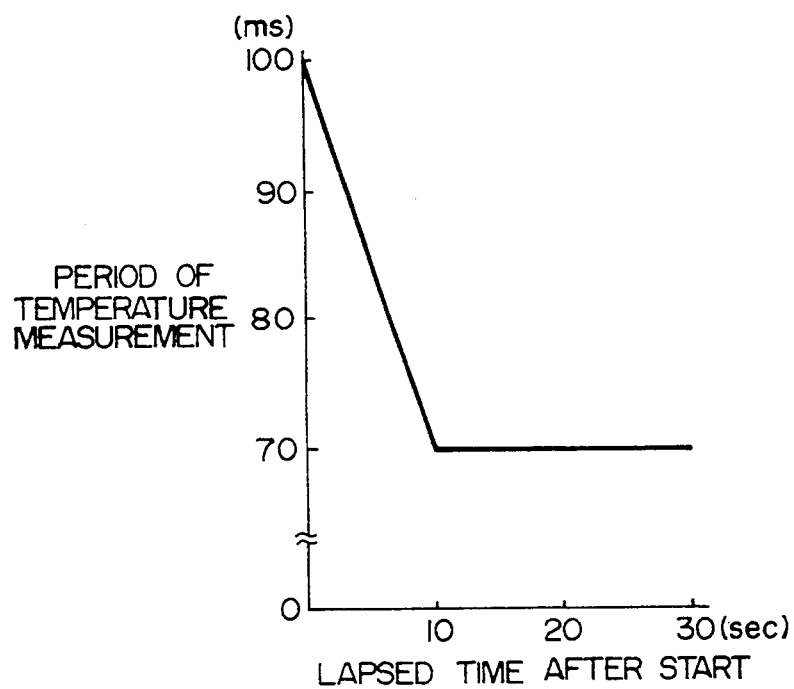
FIG. 9 is a graph showing the relation between time lapsed after the start of an engine and period of temperature detection.

In FIG. 8, at Step 200, the processing according to the flow chart is started. At the start of the engine, since the oxygen sensor S enters the active state by heating rapidly the heater 26 disposed in the sensor main body 20, temperature variations are great. For this reason, temperature determination should be effected with a short period. At Step 202, it is judged whether a period longer than a predetermined period of time t1 (e.g. 30 sec) has lapsed after the start of the engine. The reason why the predetermined period of time t1 (e.g. 30 sec) is set is that because the temperature rise characteristics of the heater 26 change, it is necessary to determine previously a period of time corresponding to the temperature rise characteristics. In the case where at Step 202 it is judged to be "NO" the procedure proceeds to Step 240 and timing of the temperature determination is judged. This timing of the temperature determination is decided on the basis of the period of the temperature determination obtained previously experimentally, as indicated in FIG. 9.

In the case where it is judged to be "NO" at this Step 240, the procedure proceeds to Step 111 in FIG. 4 in the first embodiment described previously and a positive bias command required for applying the positive voltage Vpos to the sensor main body 20 is outputted to the switching circuit 43 in the bias control circuit 40. Because the succeeding steps from Step 123 to Step 300 are identical to those described previously in the first embodiment, explanation thereof will be omitted. In the case where it is judged to be "YES" at the Step 240, the procedure proceeds to Step 112 in FIG. 4 in the first embodiment described previously and a negative bias command required for applying the negative voltage Vneg to the sensor main body 20 is outputted to the switching circuit 43 in the bias control circuit 40. Since the succeeding steps from Step 113 to Step 130 are identical to those described previously in the first embodiment, explanation thereof will be omitted.

In the case where it is judged to be "YES" at the Step 202, the procedure proceeds to Step 240 and it is judged whether or not a period of time where no temperature determination has been effected longer than a predetermined period of time t2 (e.g. 5 sec) has lapsed. The reason why the predetermined period of time t2 (e.g. 5 sec) is set is that the degree of temperature variations of the oxygen sensor S changes depending on various conditions, such as the position where the oxygen sensor S is mounted, the capacity of the heater, driving conditions, etc. and the temperature of the oxygen sensor S doesn't vary within the predetermined period of time t2 (e.g. 5 sec). On the contrary, in the case where it is judged to be "YES" at the Step 204, the procedure proceeds to Step 112 in FIG. 4 in the first embodiment described previously and a negative bias command required for applying the negative voltage Vneg to the sensor main body 20 is outputted to the switching circuit 43 in the bias control circuit 40. Because the succeeding steps from Step 113 to Step 130 are identical to those described previously in the first embodiment, explanation thereof will be omitted.

In the case where at Step 204 it is judged to be "NO" the procedure proceeds to Step 206, at which it is judged whether a period longer than a predetermined period of time t3 (e.g. 70 msec) has lapsed or not after a temperature determination has been executed. The reason why the predetermined period of time t3 (e.g. 70 msec) is set is that this is a period of time necessary for measuring the air-fuel ratio 4 or 5 times and that it is for preventing that the temperature determination is effected continuously so that the air-fuel ratio is deviated. In the case where at Step 206 it is judged to be "NO" the procedure proceeds to Step 111 in FIG. 4 in the first embodiment described previously and a positive bias command required for applying the positive voltage Vpos to the sensor main body 20 is outputted to the switching circuit 43 in the bias control circuit 40. Because the succeeding steps from Step 123 to Step 130 are identical to those described previously in the first embodiment, explanation thereof will be omitted. In the case where at Step 206 it is judged to be "YES" the procedure proceeds to the succeeding Step 208.

At Step 208, it is judged whether or not the engine is under fuel cut. In the case where at Step 208 it is judged to be "YES", since no mixture is found, although detection of the air fuel ratio is effected, the procedure proceeds to Step 214. In the case where at Step 208 it is judged to be "NO", the procedure proceeds to the succeeding Step 210. At Step 210, it is judged whether the amount of variations in the pressure in an air intake pipe or the amount of sucked air is greater than a predetermined value or not. Here judgment whether the amount of variations in the pressure in an air intake pipe or the amount of sucked air is greater than a predetermined value or not means to judge whether the engine is in a transient state or not. Consequently, not restricted to the pressure in an air intake pipe and the amount of sucked air, another parameter, e.g. aperture of throttle, speed of vehicle, number of rotations of the engine, etc. may be used, if it is a parameter, with which the transient state of the engine can be judged.

In the case where it is judged to be "YES" at Step 210 and it is confirmed that the engine is in the transient state, the procedure proceeds to Step 111 in FIG. 4 in the first embodiment described previously and a positive bias command required for applying the positive voltage Vpos to the sensor main body 20 is outputted to the switching circuit 43 in the bias control circuit 40. In the case where it is judged to be "NO" at the Step 210, the procedure proceeds to the succeeding Step 212. At this Step 212, it is judged whether the amount of variations in the air-fuel ratio is greater than a predetermined value or not. In the case where it is judged to be "YES" at the Step 212, it is supposed that there is a possibility that the temperature of the oxygen sensor has varied, the procedure proceeds to Step 214 and a negative bias command for the temperature determination is outputted. In the case where it is judged to be "NO" at the Step 212, the procedure proceeds to Step 111 in FIG. 4 in the first embodiment described previously and a positive bias command required for applying the positive voltage Vpos to the sensor main body 20 is outputted to the switching circuit 43 in the bias control circuit 40. Because the succeeding steps from Step 123 to Step 130 are identical to those described previously in the first embodiment, explanation thereof will be omitted.

After the calculating processing at Step 214, the procedure proceeds to the succeeding Step 216, where it is judged whether a predetermined period of time t4 (e.g. 30 msec) has lapsed or not. This predetermined period of time t4 (e.g. 30 msec) is identical to the predetermined period of time t1 in the first embodiment described previously. In the case where it is judged to be "YES" at this Step 216, the procedure proceeds to Step 114 in FIG. 4 in the first embodiment described previously and the converted current Ineg coming from the A-D converter 60 is considered as the current Inega. Because the succeeding steps from Step 115 to Step 130 are identical to those described previously in the first embodiment, explanation thereof will be omitted. In the case where at Step 216 it is judged to be "NO" the procedure proceeds to Step 230. At Step 230, it is judged whether the amount of variations in the pressure in an air intake pipe or the amount of sucked air is greater than a predetermined value or not, i.e. whether the engine is in a transient state or not, as described previously.

In the case where it is judged to be "NO" at the Step 230, the procedure returns to Step 216 to repeat the processing described above. In the case where it is judged to be "YES" at Step 230, the procedure proceeds to the succeeding Step 232 and at this Step 230, it is stopped to issue the negative bias command. Thereafter, the procedure proceeds to Step 111 in FIG. 4 in the first embodiment described previously to issue the positive bias command. Since the succeeding steps from Step 123 to Step 130 are identical to those described previously in the first embodiment, explanation thereof will be omitted. As explained above, in this second modified example, because the temperature determination is effected after the oxygen sensor S has become to be in the active state and the unstable state has been removed after the start of the engine, it is possible to estimate the saturation current Inegs with a higher precision.

Figure 10:
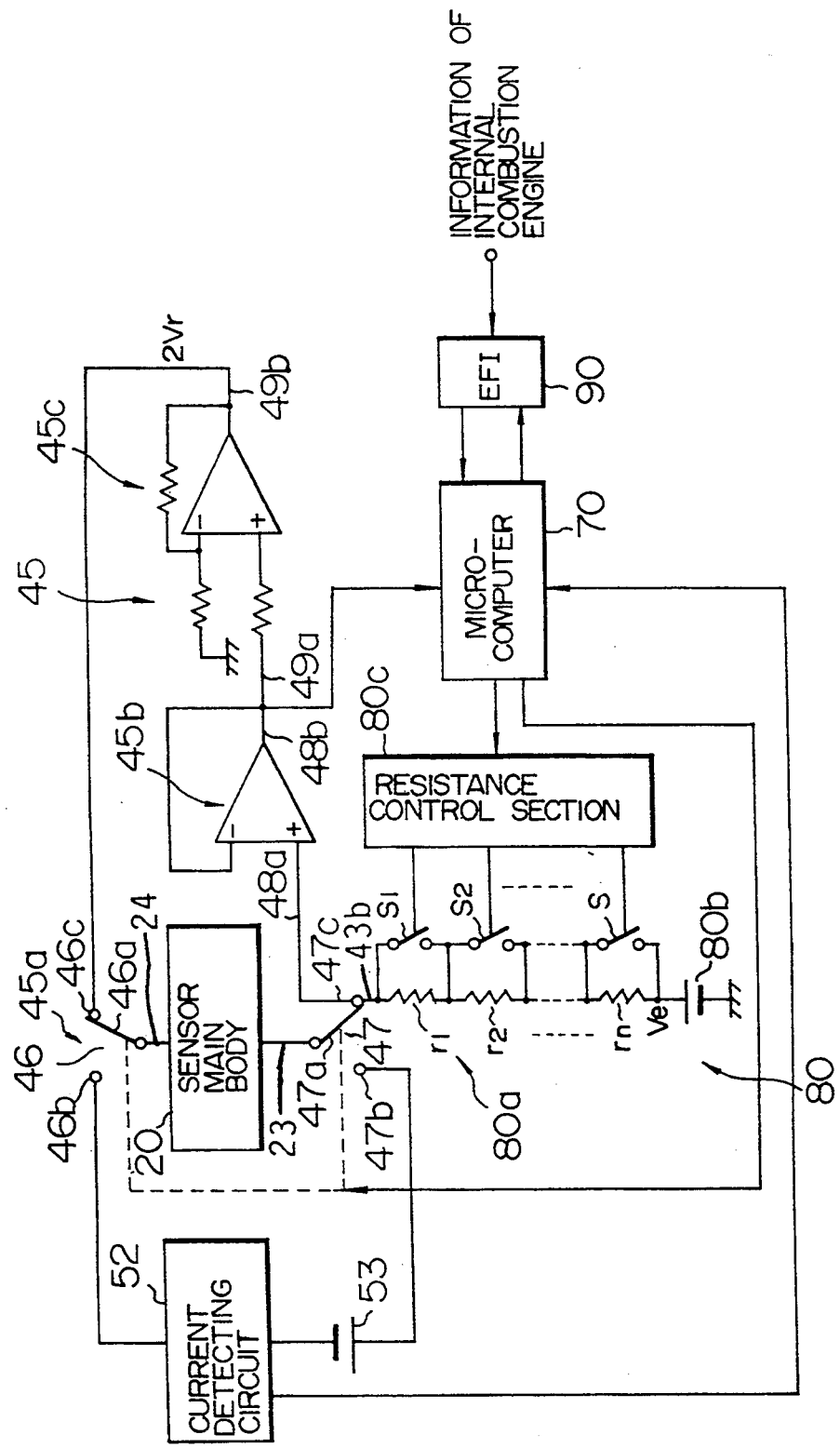
FIG. 10 is a block diagram showing a second embodiment of the present invention.

Now a second embodiment of the present invention will be explained, referring to FIGS. 10 and 11. As indicated in FIG. 10, this oxygen concentration measuring device is provided with a voltage forming circuit 45. This voltage forming circuit 45 consists of a linked switching circuit 45a, an operational amplifier 45b and another operational amplifier 45c. The linked switching circuit 45a consists of electronic two-sided type switches 46 and 47 switched while being linked with each other. The atmosphere side electrode layer 24 and the exhaust gas side electrode layer 23 are connected with a switching contact 46a of the switch 46 and a switching contact 47a of the switch 47, respectively. Further, the linked switching circuit 45a is constructed so as to close the switching contact 46a of the switch 46 at a fixed contact 46b and at the same time the switching contact 47a of the switch 47 at a fixed contact 47b and on the other hand to close the switching contact 46a of the switch 46 at another fixed contact 46c and at the same time the switching contact 47a of the switch 47 at another fixed contact 47c under control by the microcomputer 70 described later. Hereinbelow a state where the switching contact 46a of the switch 46 is closed with a fixed contact 46b and at the same time the switching contact 47a of the switch 47 is closed with a fixed contact 47b is called a left side closing state of the linked switching circuit 45a, while a state where the switching contact 46a of the switch 46 is closed with a fixed contact 46c and at the same time the switching contact 47a of the switch 47 is closed with a fixed contact 47c is called a right side closing state of the linked switching circuit 45a.

The operational amplifier 45b is connected with the fixed contact 47c of the switch 47 and an output terminal of a resistance control circuit 80 stated later by its non-inverted input terminal and this operational amplifier 45b outputs a control voltage Vr produced at the output terminal 43b of the resistance control circuit 80 as it is through its output terminal 43b. The gain of this operational amplifier 45b is "1". Since no current flows through the non-inverted input terminal 48a, a same current flows both through the sensor main body 20 and the resistance control circuit 80. On the other hand, the operational amplifier 45c is connected with the output terminal 48b of the operational amplifier 45b by its non-inverted input terminal 49a and an output terminal 49b of this operational amplifier 45c is connected with the fixed contact 46c of the switch 46. The gain of this operational amplifier 45c is "2". In this way it amplifies the output control voltage Vr to an applied voltage 2Vr, which is amplified by a factor 2, to apply it to the fixed contact 46c of the switch 46. In this way it is possible to apply the control voltage Vr to the sensor main body 20 through the linked switching circuit 45a. This means that both the voltage applied to the sensor main body 20 and the output control voltage of the resistance control circuit 80 are Vr.

The current detecting circuit 52 is connected with the fixed contact 46b of the switch 46 by its current terminal of one side and a current terminal of other side of the current detecting circuit 52 is connected with the fixed contact 47b of the switch 47 through a DC power source 53. The DC power source 53 outputs the negative applied voltage Vneg so as to make current flow in a direction of polarity indicated in FIG. 10 (corresponding to the direction to bias negatively the sensor main body 20) through the linked switching circuit 45a, the current detecting circuit 52 and the solid electrolyte layer 22. In this way the current detecting circuit 52 determines the current (hereinbelow called current Ineg) flowing through the sensor main body 20 on the basis of the applied voltage Vneg.

Figure 11:
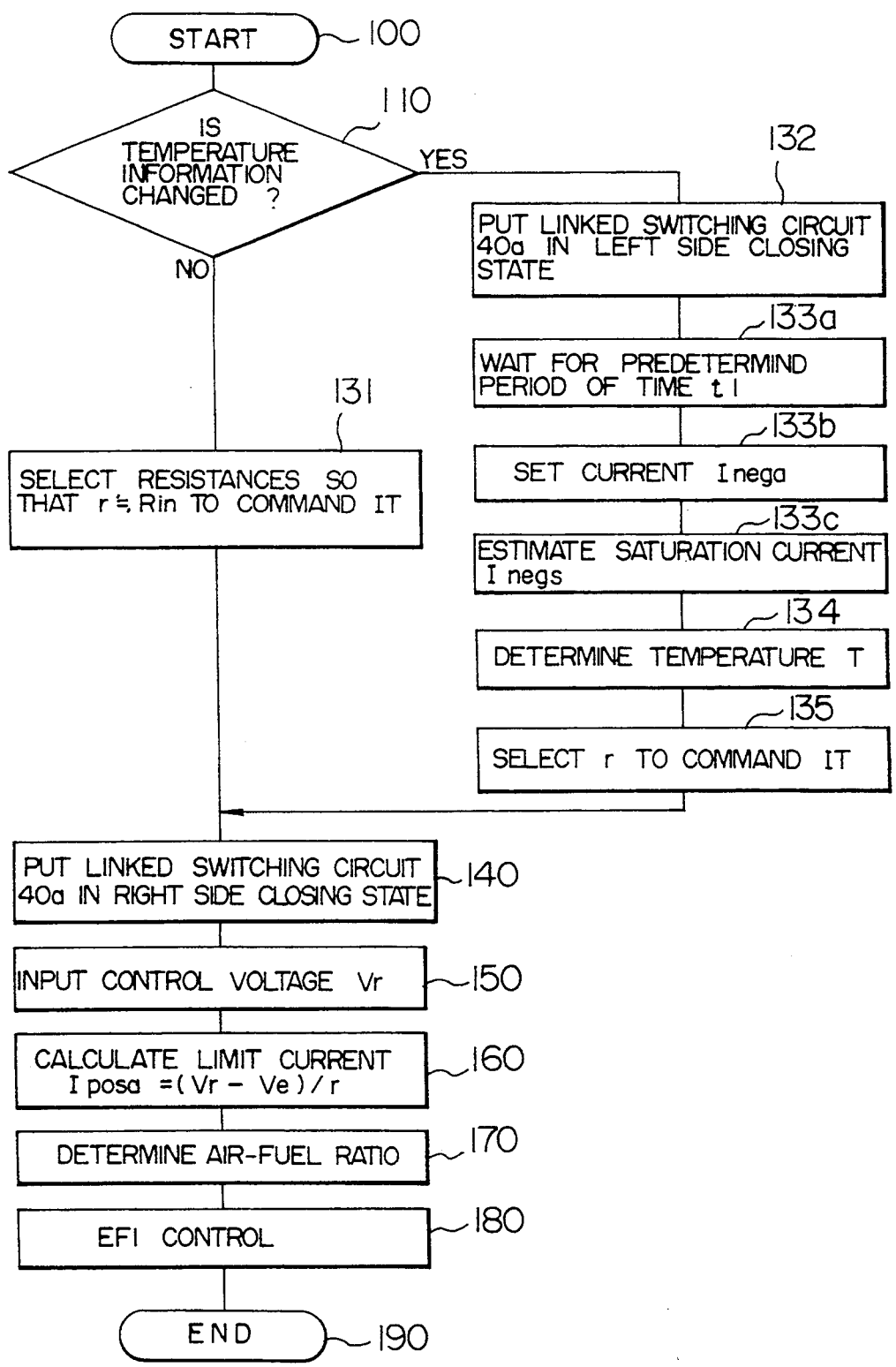
FIG. 11 is a flow chart showing the operation of the microcomputer indicated in FIG. 10.

The microcomputer 70 executes the computer program according to the flow chart indicated in FIG. 11 in collaboration with the voltage forming circuit 45 and the current detecting circuit 52. In this execution it effects calculating processing necessary for driving the resistance control circuit 80 so as to control it and the fuel injection control device 90 (hereinbelow called EFI 90). The computer program is stored previously in the ROM of the microcomputer 70.

The resistance control circuit 80 consists of a resistance selecting circuit 80a, a DC power source 80b and a resistance control section 80c. The resistance selecting circuit 80a consists of a series of resistances r1, r2, ..., rn connected in series and normally open type electronic switches s1, s2, ..., sn, each of which is connected with each corresponding switch in parallel. The resistance r1 is connected with the positive side electrode of the DC power source 80b through the other resistances r2, ..., rn at an end thereof and the other end of this resistance r1, i.e. the output terminal of the resistance control circuit 80, is connected with the fixed contact 47c of the switch 47. Each of the different electronic switches s1, s2, ..., sn, is closed selectively under control by the resistance control section 80c to short-circuit each corresponding resistance r1, r2, ..., rn.

Figure 12:
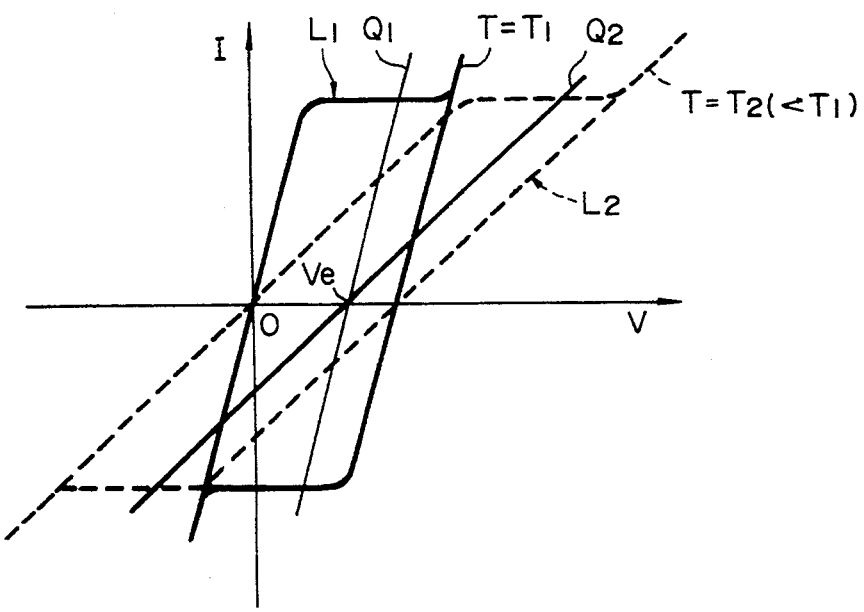
FIG. 12 is a diagram for explaining the relation between current-voltage characteristics and DC voltage Ve in the second embodiment.

The DC power source 80b outputs a DC voltage Ve. This DC voltage Ve plays a role of translating parallelly each of inclined straight line portions passing through the origin O of two characteristic graphs L1 and L2 in FIG. 12 in the positive direction of the voltage axis V by the DC voltage Ve to transform them into inclined straight lines Q1 and Q2, respectively. That is, because both the voltage applied to the sensor main body 20 and the output control voltage are equal to Vr, as described previously, and also currents flowing therethrough are equal to each other, working points of the current and the voltage are on the inclined straight line Q1 at the temperature T1 and on the inclined straight line Q2 at the temperature T2. The intercept and the gradient of each of the inclined straight lines Q1 and Q2 with respect to the voltage axis are Ve and (1/Rin), respectively. Further, because the input resistance of the operational amplifier 45b is very great, when the linked switching circuit 45a is in the right side closing state, since the DC current from the operational amplifier 45c flows through the sensor main body 20. the resistance selecting circuit 80a and the DC power source 80b, the control voltage Vr produced at the output terminal of the resistance control circuit 80a is determined by the DC power source Ve and a selective resultant resistance r of the resistance selecting circuit 80a. The resistance control section 80c controls the different electronic switches s1, s2, ..., sn to select the resultant resistance r of the resistance selecting circuit 80a under control by the microcomputer 70. In addition, the EFI 90 controls fuel injection, corresponding to the information of the internal combustion engine such as amount of exhaust gas, number of rotations, flow rate of sucked air, air intake pipe pressure, temperature of cooling water, etc.

In the second embodiment thus constructed, it is supposed that the microcomputer 70 executes repeatedly the computer program according to the flow chart indicated in FIG. 11 after having started the execution of the computer program at Step 100. Further, at the present stage, it is supposed that the oxygen sensor S is in the heated state of the heater 26. Unless the information of the internal combustion engine such as amount of exhaust gas, number of rotations, flow rate of sucked air, air intake pipe pressure, temperature of cooling water, etc. of the internal combustion engine 10 coming from the EFI 90 is changed suddenly, under judgment that temperature information of the sensor main body 20 is unnecessary, judgment to be "NO" is repeated at Step 110.

In such a state, the microcomputer 70 makes the computer program proceed to Step 131 or Step 140 and the followings in FIG. 11. In such a case, the microcomputer 70 outputs a command of determining and selecting the resultant resistance r of the resistance selecting circuit 80a to the resistance control section 80c at Step 131 so as to be approximately equal to the actual internal resistance Rin of the sensor main body 20 represented by the gradient of the inclined straight line Q1. For this purpose, the resistance control section 80c controls the different electronic switches s1, s2, ..., sn in the resistance selecting circuit 80a by opening or closing them so that the resultant resistance r of the resistance selecting circuit 80a is approximately equal to the actual internal resistance Rin of the sensor main body 20. Consequently, the resistance selecting circuit 80a selects the resultant resistance r so as to be approximately equal to the actual internal resistance Rin.

Then the microcomputer 70 outputs a command necessary for turning over the linked switching circuit 45a to the right side closing state to the same linked switching circuit 45a at Step 140. In this way, the linked switching circuit 45a is turned over to the right side closing state. When the DC current from the operational amplifier 45c flows through the switch 46, the sensor main body 20, the switch 47, the resistance selecting circuit 80a and the DC power source 80b, the resistance selecting circuit 80a produces the control voltage Vr at the output terminal thereof; the operational amplifier 45b outputs the control voltage Vr; and the operational amplifier 45c outputs the applied voltage 2Vr. For this reason a half of the applied voltage 2Vr is applied to the sensor main body 20.

Further, when the operational amplifier 45b outputs the control voltage Vr as described above, the control voltage Vr is inputted to the microcomputer 70 at Step 150, which calculates the limit current Iposa on the basis of the following Eq. (4), corresponding to the resultant resistance r at Step 131 and the control voltage Vr at Step 150;

$$Iposa = (Vr - Ve)/r \qquad (4)$$

Figure 5C:
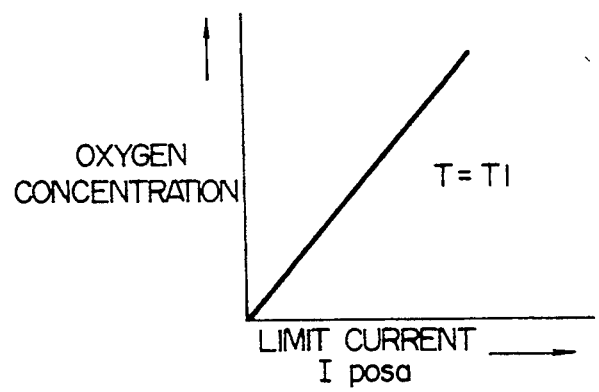
FIG. 5C is a graph showing the relation between oxygen concentration and limit current.

The equation representing this relationship is stored previously in the ROM of the microcomputer 70. Then the microcomputer 70 determines the oxygen concentration, i.e. air-fuel ratio, corresponding to the limit current Iposa, on the basis of the oxygen concentration-limit current data indicated in FIG. 5C at Step 170. In such a case, the oxygen concentration-limit current data indicated in FIG. 5C are stored previously in the ROM of the microcomputer 70 as data for specifying a linear relationship between the oxygen concentration in the exhaust gas, i.e. air-fuel ratio, and the limit current of the sensor main body 20. When the air-fuel ratio is determined in this way, the microcomputer 70 executes calculating processing necessary for fuel injection control of the EFI 90 at Step 180, taking the same air-fuel ratio into account. In this way the EFI 90 controls fuel injection into the internal combustion engine 10 on the basis of the calculating processing.

When the information of the internal combustion engine 10 coming from the EFI 90 such as amount of exhaust gas, number of rotations, flow rate of sucked air, air intake pipe pressure, temperature of cooling water, etc. is changed suddenly, under judgment that temperature information has been changed, the microcomputer 70 judges to be "YES" at Step 110 and outputs a command necessary for turning over the linked switching circuit 45a to the left side closing state to the same linked switching circuit 45a at Step 132. In this way the linked switching circuit 45a is turned over to the left side closing state. Then the current Ineg from the DC power source 53 flow in the current detecting circuit 52 through the switch 47, the sensor main body 20 and the switch 46. After the calculating processing at Step 132 as described above, the microcomputer 70 waits for a predetermined period of time t1 at Step 133a. In such a case, the predetermined period of time t1 is determined as follows. After the moment when the sensor main body 20 has been negatively biased, the current Ineg increases exponentially, as indicated by the full and broken lines in FIG. 5B. Consequently, in the case where the current Ineg is determined, waiting until this current Ineg is saturated as by the prior art techniques, the determination time of the air-fuel ratio succeeding it is also retarded. For this reason, the saturation current Inegs of the current Ineg is estimated at a point of time in the increasing process of the current Ineg by using the value of the current Inega at that point of time. It can be understood that the determination time of the air-fuel ratio is advanced in this way. Therefore, the predetermined period of time t1 is selected so as to be a proper period of time when variation tendency in the current Ineg is maintained relatively high after the moment where the sensor main body 20 has been negatively biased and stored in the ROM of the microcomputer 70.

When the wait at Step 133a is terminated, the microcomputer 70 considers the detected current Ineg from the current detecting circuit 52 to be the current Ineg at Step 133b and estimates the saturation current Inegs corresponding to the same current Inega at Step 133c on the basis of the transient phenomenon equation representing the relation between the current Ineg and the applied voltage Vneg. In such a case, the transient phenomenon equation is constructed by using conditions at the time where the sensor main body 20 is negatively biased as initial conditions and stored previously in the ROM of the microcomputer 70. Thereafter the microcomputer 70 determines the temperature of the sensor main body 20 at Step 134, corresponding to the estimated saturation current Inegs, on the basis of the current-temperature characteristic data.

Then the microcomputer 70 determines the resultant resistance r at Step 135 corresponding to the determined temperature T at Step 134 on the basis of resistance-temperature characteristic data representing the relation between the resultant resistance r to be selected by the resistance selecting circuit 80a and the temperature T and outputs a command of selecting the resultant resistance r thus determined to the resistance control section 80c. For this purpose, the resistance control section 80c controls the different electronic switches s1, s2, . . . , sn in the resistance selecting circuit 80a by opening or closing them so that the resultant resistance r of the resistance selecting circuit 80a is the determined resultant resistance. Consequently the resistance selecting circuit 80a selects resistances so that the resultant resistance thereof represent the determined resultant resistance r. The resistance-temperature characteristic data are data for specifying inversely proportionally the relation between the resultant resistance r and the temperature T of the sensor main body 20 and these resistance-temperature characteristic data are stored previously in the ROM of the microcomputer together with the current-temperature characteristic data.

When the calculating processing at Step 135 is terminated in this way, the microcomputer 70 outputs a command necessary for turning over the linked switching circuit 45a to the right side closing state to the same linked switching circuit 45a at Step 140 to turned over the linked switching circuit 45a to the right side closing state. When the DC current from the operational amplifier 45c flows through the switch 46, the sensor main body 20, the switch 47, the resistance selecting circuit 80a and the DC power source 80b, the resistance selecting circuit 80a produces the control voltage Vr at the output terminal thereof; the operational amplifier 45b outputs the control voltage Vr; and the operational amplifier 45c outputs the applied voltage 2Vr. For this reason a half of the applied voltage 2Vr is applied to the sensor main body 20.

Further, when the operational amplifier 45b outputs the control voltage Vr, which is inputted to the microcomputer 70 at Step 150, and the microcomputer 70 calculates the limit current Iposa at Step 160, corresponding to the resultant resistance r at Step 131 and the control voltage Vr at Step 150, on the basis of the relationship given by Eq.(4). Then the microcomputer 70 determines the oxygen concentration, i.e. the air-fuel ratio, at Step 170, corresponding to the limit current Iposa on the basis of the oxygen concentration-limit current data and executes calculating processing required for the fuel injection control of the EFI 190 at Step 180, taking the air-fuel ratio thus obtained into account. In this way the EFI 90 effects the control of fuel injection into the internal combustion engine 10 on the basis of the calculating processing.

As explained above, paying attention to the fact that the limit current remains almost unchanged, even if the gradient of the inclined straight line portion passing through the origin O of the current-voltage characteristics of the sensor main body 20 is varied, accompanied by variations in the actual internal resistance Rin of the sensor main body 20, the resistance control circuit 80 produces the resultant resistance r on the basis of the calculating processing at Step 131 or at Steps 132 to 135 so as to be approximately equal to the actual internal resistance Rin of the sensor main body 20 specified by the current-voltage characteristics at the actual temperature and the limit current Iposa is obtained under calculating processing at Steps 140 to 160 in relation with this resultant resistance r. For this reason, even if the temperature of the sensor main body 20 is lowered, without waiting for heating control thereof, it is possible to realize a period of time where the air-fuel ratio can be determined early by calculating the limit current flowing through the sensor main body 20 specified by the current-voltage characteristics at the actual temperature. In such a case, since the temperature of the sensor main body 20 is determined only when it is judged at Step 110 that temperature information of the sensor main body 20 has been changed, the period of time where the air-fuel ratio can be measured can be longer than that obtained in the case where the temperature is determined periodically as by the prior art techniques.

Further, since for determining the temperature of the sensor main body 20 the saturation current Inegs is estimated by using the current Inega at a point of time (after the predetermined period of time t1 has lapsed) before the current Ineg flowing through the sensor main body 20 finishes to rise after the sensor main body 20 has been negatively biased by applying the voltage Vneg to the sensor main body 20 and the temperature of the sensor main body 20 is determined by using this saturation current Inegs thus estimated, it is possible to realize early a succeeding period of time where the air-fuel ratio can be determined, similarly to the first embodiment.

Figure 13:
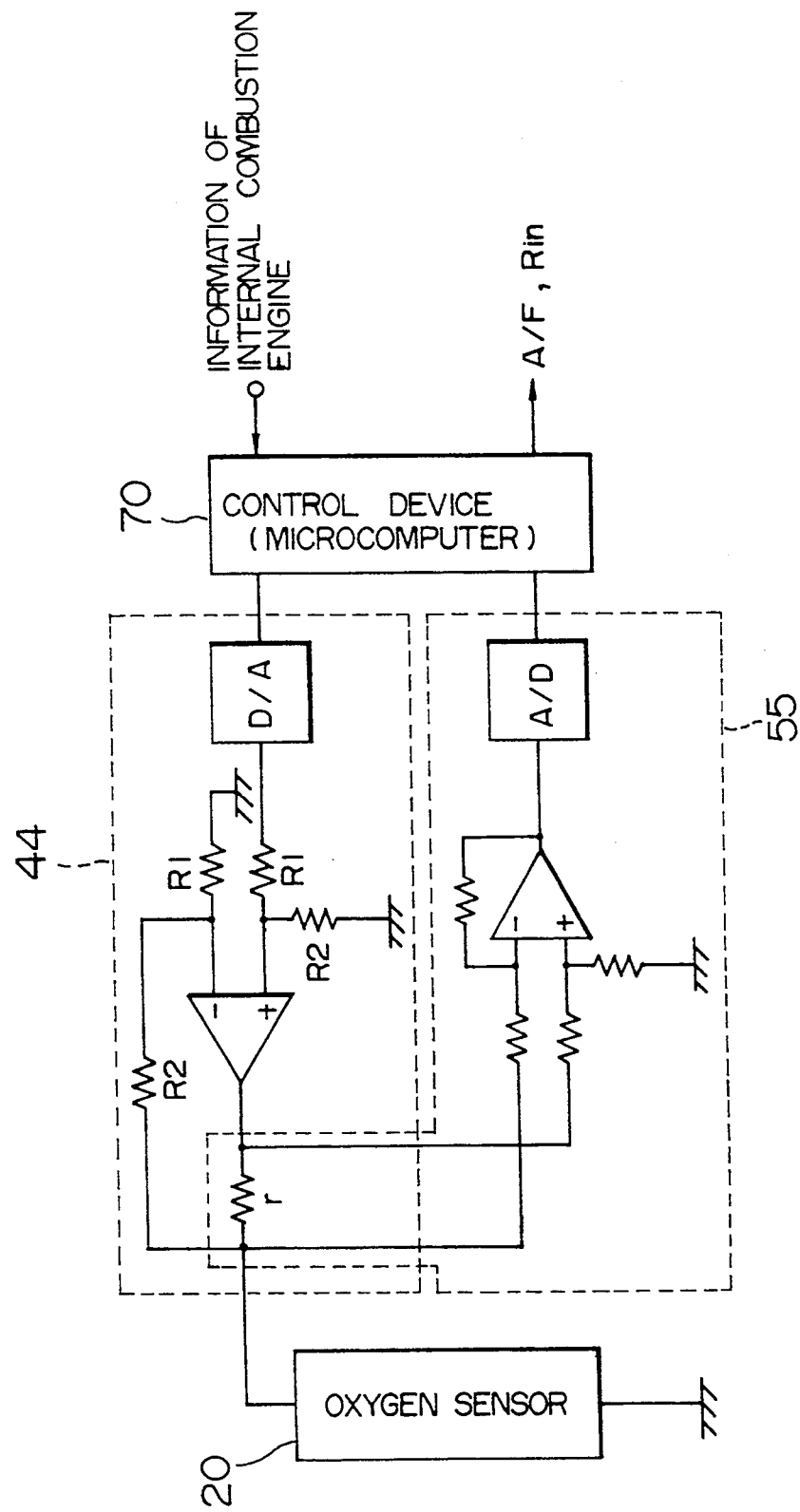
FIG. 13 is a block diagram showing a third embodiment of the present invention.

Now a third embodiment of the present invention will be explained, referring to FIGS. 13 to 20. In this third embodiment, when determining the air-fuel ratio, concerning temperature variations of the oxygen sensor, the voltage applied to the oxygen sensor is not varied continuously, corresponding to the temperature of the oxygen sensor, but an applied voltage is determined for each of temperature regions so that the air-fuel ratio can be measured, even if the temperature varies. FIG. 13 is a block diagram indicating this third embodiment, in which a voltage is applied to the oxygen sensor 20 by a voltage applying section 44 and current flowing at that time therethrough is determined by a current detecting section 55. The control device (microcomputer) 70 gives the voltage applying section 44 an instruction on the applied voltage appropriately selected on the basis of the current intensity determined by the current detecting section 55 and the internal resistance of the oxygen sensor 20 measured by other detecting means.

Figure 14:
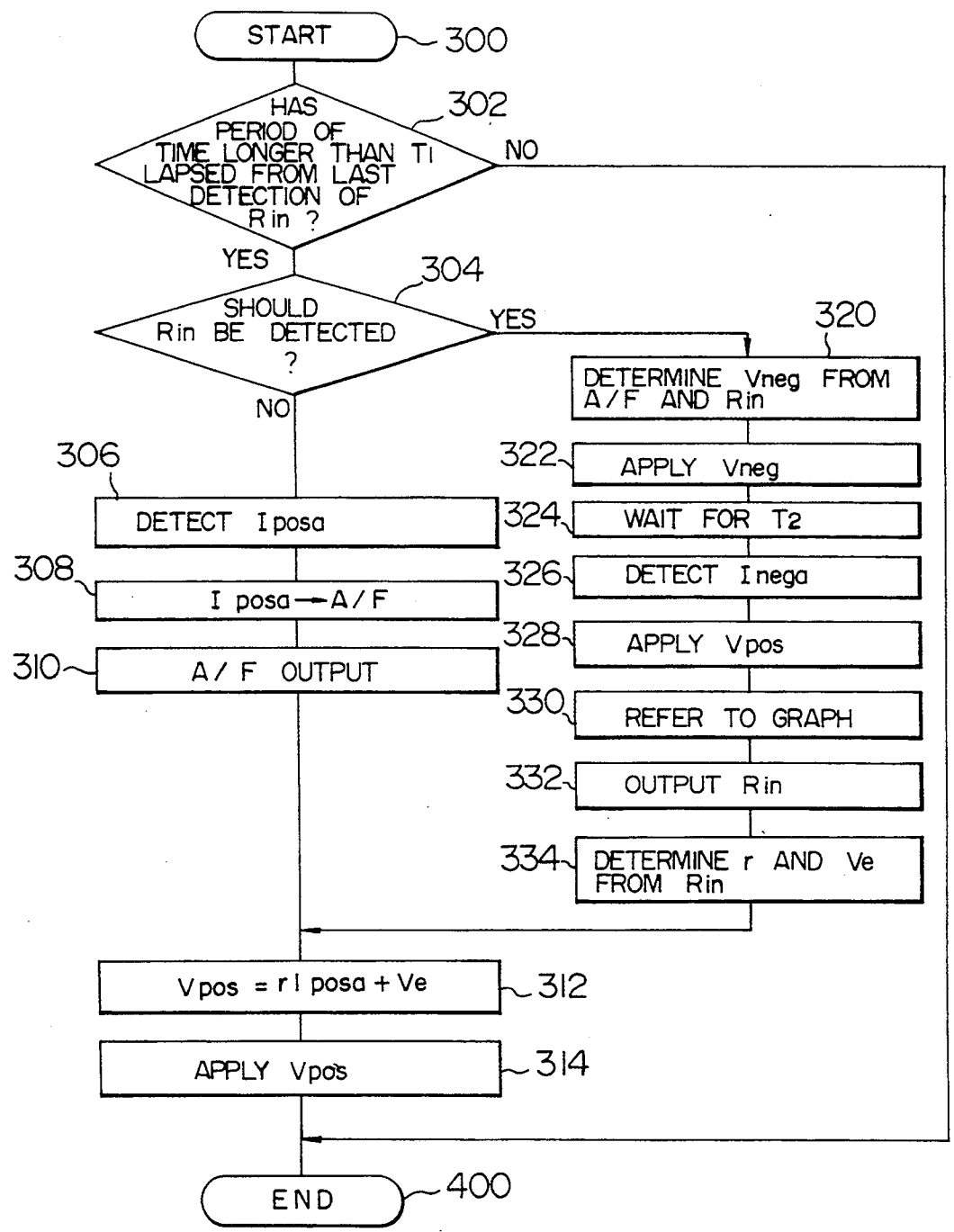
FIG. 14 is a flow chart showing the operation of the microcomputer in the third embodiment.

In the third embodiment thus constructed, it is supposed that the microcomputer 70 executes repeatedly the computer program according to the flow chart indicated in FIG. 14 every 10 msec after having started the execution of the computer program at Step 300. After the execution has been started at Step 300 at first, it is judged at Step 302 whether a period of time longer than a predetermined period of time T1 (e.g. 30 msec) has lapsed or not, measured from the last determination of the internal resistance Rin of the oxygen sensor, if it is shorter than the predetermined period of time T1, it is judged to be "NO" and the operation of the control device is terminated as it is. If it is longer than the predetermined period of time T1 or directly after the start of the control device, it is judged to be "YES".

When it is judged to be "YES" at Step 302, the procedure proceeds to the following Step 304. At this Step 304 it is judged whether it is necessary to determine the internal resistance Rin of the oxygen sensor 20 by using the information of the internal combustion engine such as amount of exhaust gas, number of rotations, flow rate of sucked air, air intake pipe pressure, temperature of cooling water, etc. If it is judged that it is necessary to determine the internal resistance Rin of the oxygen sensor 20, it is judged to be "YES" and the procedure proceeds to the following Step 320. On the contrary, if it is judged that it is necessary to determine the internal resistance Rin of the oxygen sensor 20, it is judged to be "NO" and the procedure proceeds to the following Step 306.

Figure 15:
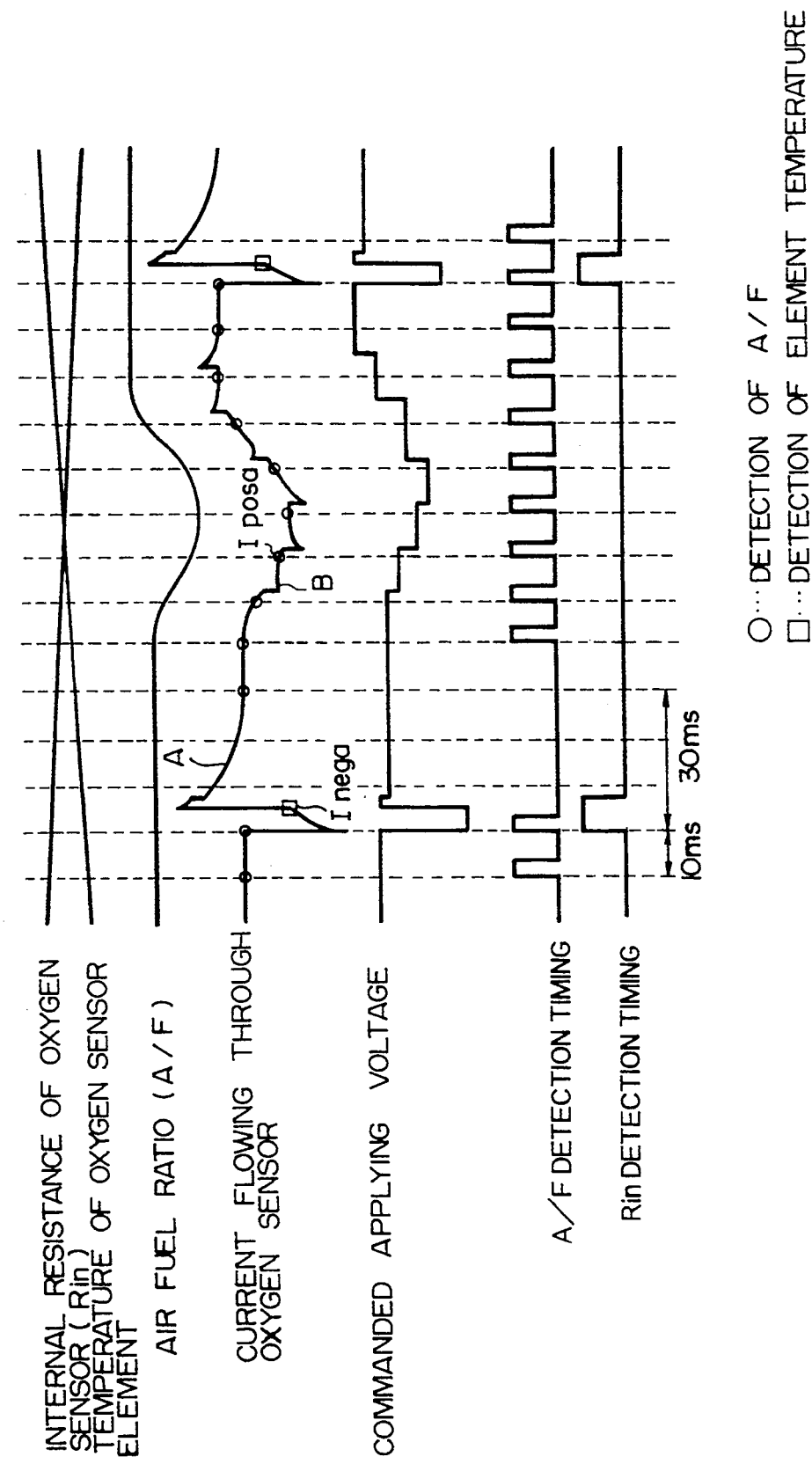
FIG. 15 is a timing chart showing the operation of the microcomputer in the third embodiment.
Figure 16:
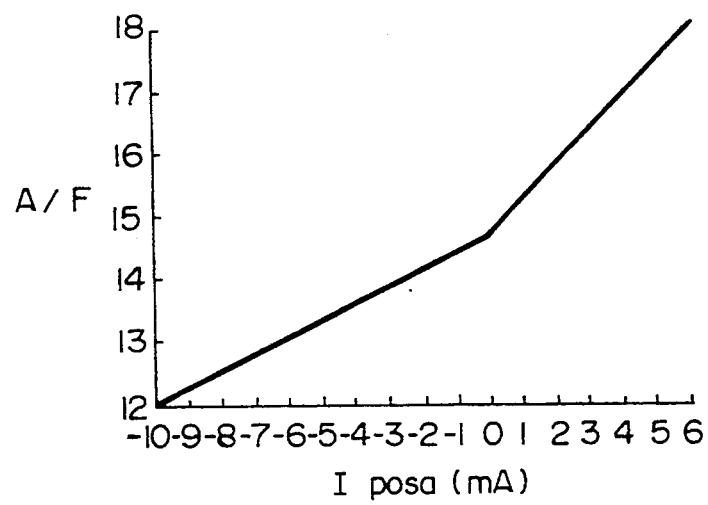
FIG. 16 is a graph showing the relation between limit current intensity and air-fuel ratio.

FIG. 15 is a timing chart indicating the operations described above. In FIG. 15, an interval 10 msec for determining the air-fuel ratio in synchronism with an internal clock of the microcomputer 70 and a period of time 30 msec from the moment where the determination of the internal resistance Rin is begun to the moment where a succeeding air fuel ratio is determined are decided as follows. That is, the voltage applied to the oxygen sensor 20 (command applied voltage) is varied as indicated in FIG. 15, corresponding to the intensity of the current flowing through the oxygen sensor 20. In this case, when the command applied voltage is varied, the current flowing through the oxygen sensor 20 has characteristic features that it rises once and then converged exponentially, as indicated by A and B parts in FIG. 15. Therefore, in order to determine the limit current corresponding to the air-fuel ratio with a high precision, it is necessary to determine a succeeding air fuel ratio after a certain period of time, measured from the moment where the voltage has been varied. Since the time necessary for converging the current depends principally on the amount of variations in the voltage, it about 25 msec (A part in FIG. 15 after the determination of the internal resistance Rin and about 10 msec (B part in FIG. 15) after the determination of the air-fuel ratio. Consequently, if succeeding determinations of the internal resistance Rin and the air-fuel ratio are effected after 30 msec and 10 msec, respectively, the air-fuel ratio can be determined with a high precision.

Hereinbelow the manner in which the command applied voltage is varied when the internal resistance Rin and the air-fuel ratio are varied and how the internal resistance Rin and the air-fuel ratio are determined will be described. In the flow chart indicated in FIG. 14, if it is judged to be "NO" at Step 304, the procedure proceeds to Step 306, at which the limit current Iposa of the oxygen sensor 20 is determined by the current detecting section 55 in FIG. 13. After the limit current Iposa of the oxygen sensor 20 has been determined at this Step 306, the procedure proceeds to Step 308. At Step 308, the air-fuel ratio is determined at Step 308, starting from the limit current Iposa determined at Step 306, on the basis of a graph for converting the limit current Iposa into the air fuel ratio in FIG. 16, and a value thus obtained is outputted at the succeeding Step 310. Then the procedure proceeds to Step 312 and the command applied voltage Vpos is calculated at this Step 312, corresponding to the limit current Iposa determined at Step 306, on the basis of the relation given by the following Eq. (5);

$$Vpos = rIposa + Ve \quad (5)$$

Figure 17:
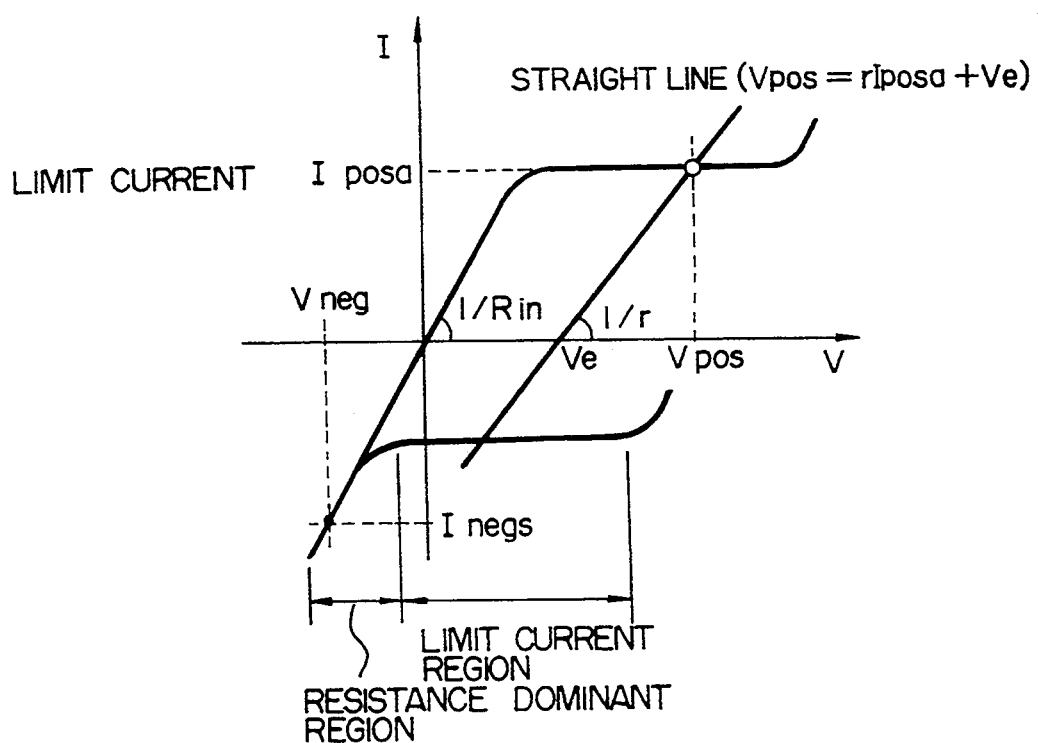
FIG. 17 is a graph indicating limit current-voltage characteristics for the oxygen sensor, which shows concept of a method for determining the voltage (Vpos) applied when detecting the air-fuel ratio.

Then the procedure proceeds to Step 314. At this Step 314, the microcomputer 70 gives the voltage applying section 44 indicated in FIG. 13 a command to apply the command applied voltage Vpos obtained at Step 312. How the parameters r and Ve used in the calculation of Vpos are decided will be described later. FIG. 17 indicates the fundamental concept thereof.

FIG. 17 indicates characteristics of the oxygen sensor. If Vpos is not in the voltage region, in which the value of the limit current appears, i.e. in the limit current region, no precise air-fuel ratio can be determined. This limit current region is translated parallelly by the limit current Iposa and the amount of the translation is determined by the internal resistance Rin of the oxygen sensor 20. Therefore, if it is desired that the air-fuel ratio can be determined in a wide range, it is necessary to vary the command applied voltage Vpos, depending on the value of the limit current Iposa and the ratio r of Vpos to Iposa should be a value close to the internal resistance Rin. Further, when the V intercept (intersection with the voltage V axis) Ve of the Vpos straight line is set in the neighborhood of the center (0.3~0.5 V) of the limit current region at the theoretical air fuel ratio (Iposa=0), tolerable errors for the determination of the internal resistance Rin in order that Vpos is in the limit current region in a lean domain (Iposa>0) or a rich domain (Iposa<0) are enlarged.

Figure 18A:
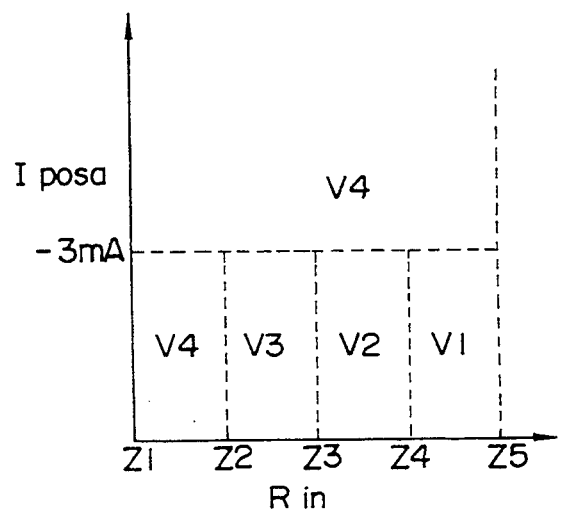
FIGS. 18A and 18B are graphs used for determining the voltage (Vneg) applied when detecting the internal resistance (Rin) of the oxygen sensor, FIG. 18A being a graph showing the relation among limit current, internal resistance and applied voltage of the oxygen sensor, FIG. 18B being a graph used for determining the applied voltage, starting from the limit current and the internal resistance of the oxygen sensor.
Figure 18B:
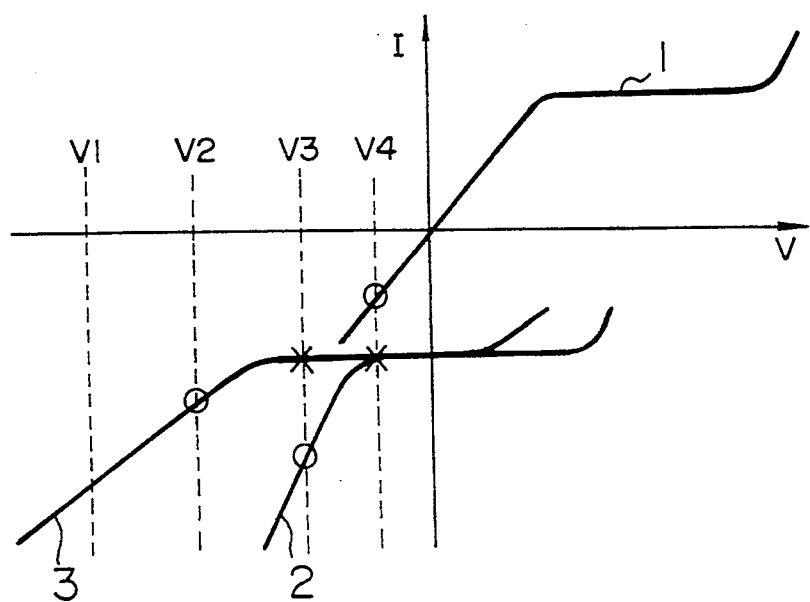

At Step 320, the voltage Vneg applied to the oxygen sensor 20 for determining the internal resistance Rin is determined according to FIG. 18A by using values determined at the last time of the internal resistance Rin and the limit current Iposa. The reason why Vneg is determined will be explained below. In FIG. 18B, in characteristics 1 of the oxygen sensor when exhaust gas is lean, since all the regions lower than V4 are resistance-dominant, any one of V1 to V4 may be used without problem (in the present third embodiment, V4 for which the sensor current is smallest is used for Vneg). However, in characteristics 2 and 3 of the oxygen sensor when the exhaust gas is rich, since the limit current region is on the negative voltage side and the position thereof varies, depending on the internal resistance Rin of the oxygen sensor, if Vneg=V4 for characteristics 2 or if Vneg=V3, V4 for characteristics 3, it is not possible to find the gradient in the resistance-dominant region and determination precision of the internal resistance Rin of the oxygen sensor is worsened. For this reason, Z1 to Z5 in FIG. 18A are determined appropriately so as to be able to select V3 for characteristics 2 and V2 for characteristics 3. It is to stabilize control characteristics in the neighborhood of the limit current Iposa=0 mA (theoretical air fuel ratio) and the boundary of the limit current Iposa is set at −3 mA.

When Vneg is determined at Step 320 as described above, then the procedure proceeds to Step 322. At this Step 322, the microcomputer 70 gives the voltage applying section 44 in FIG. 13 a command to apply Vneg to the oxygen sensor. Then the procedure proceeds to Step 324. At this Step 324 the procedure waits for a predetermined period of time T2 (e.g. 5 msec). This predetermined period of time T2 corresponds to t1 in the first embodiment. After the predetermined period of time T2 has lapsed, the procedure proceeds to Step 326. At this Step 326, the current Inegs in the course of convergence is determined and at the succeeding Step 328 the Vpos which was applied at the last time is applied to the oxygen sensor 20 for a while. This is for preventing that processings at the succeeding steps 330 to 314 takes long time, and when the voltage Vpos is applied to the oxygen sensor first at Step 314, convergence in the current converging waveform A of the current flowing through the oxygen sensor indicated in FIG. 15 is retarded, which worsens precision of a succeeding determination of the air-fuel ratio. In the case where there is no special problem concerning performance of the computer, characteristics of the oxygen sensor, etc., this Step 328 may be omitted.

Figure 19:
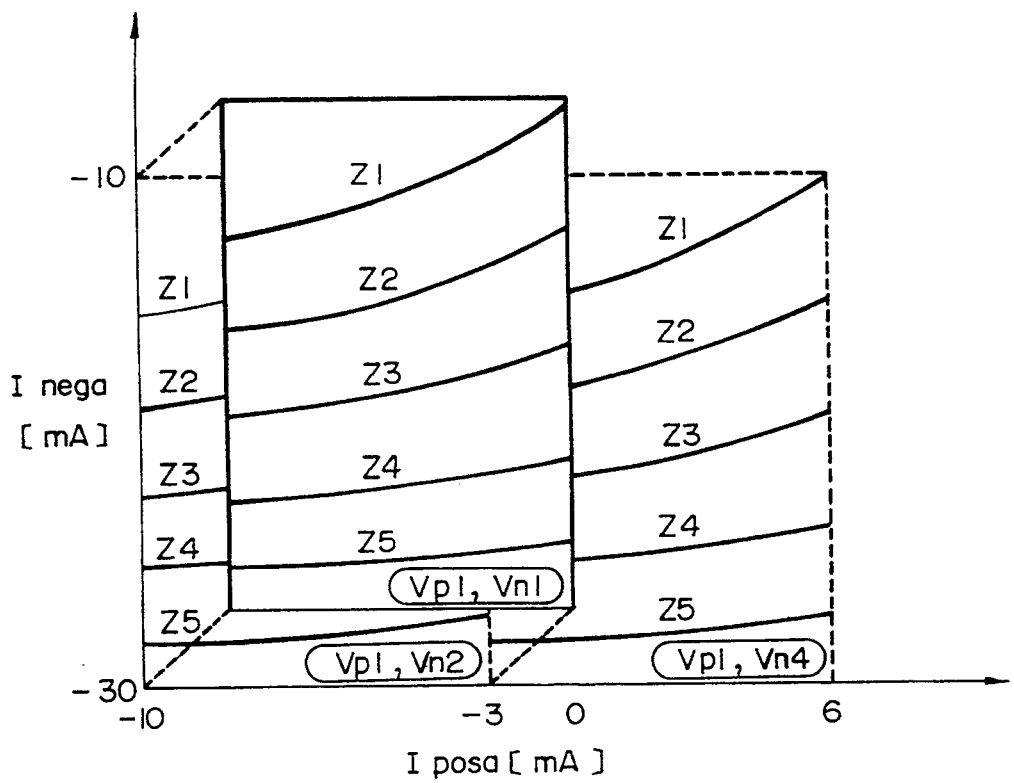
FIG. 19 is a graph used for estimating the internal resistance (Rin) of the oxygen sensor, starting from the detected current intensity (Inega)

Then the procedure proceeds to Step 330, at which the internal resistance Rin of the oxygen sensor 20 is determined on the basis of the graph indicated in FIG. 19 by using the current Inega in the course of convergence determined at Step 326. This graph is constructed by a number of sheets of two-dimensional graph of Iposa and Inega, which number is a number of conceivable combinations of the Vpos straight line and Vneg (the number of sheets of graph increasing proportionally to the number of Vpos straight lines and the number of Vneg). Parameters used in the graph representing the internal resistance Rin of the oxygen sensor indicated in FIG. 19 are decided for the following reason. That is, the Ineg waveform in FIG. 5B in the first embodiment described previously is determined by 4 parameters, i.e. Vpos, Vneg, Ipos and Ineg. Further, since the internal resistance Rin of the oxygen sensor is given by a relation Rin=Vneg/Ineg according to FIG. 17, the Ineg waveform can be decided also by 4 parameters of Vpos, Vneg, Ipos and Rin. Consequently, if the relation between the 4 parameters described above, i.e. Vpos, Vneg, Ipos and Ineg, and the value of Ineg on the waveform of Ineg is traced in the form of a graph, as indicated in FIG. 19, the internal resistance Rin of the oxygen sensor can be obtained by using Vpos, Vneg, Ipos and Inega according to the graph. Further, in the case where the relation between each of these parameters and the internal resistance Rin can be approximated by using a certain formula, it is conceivable to reduce the amount of data for the graph by omitting the relevant parameter and correcting the internal resistance Rin by using the approximation formula.

Figure 20:
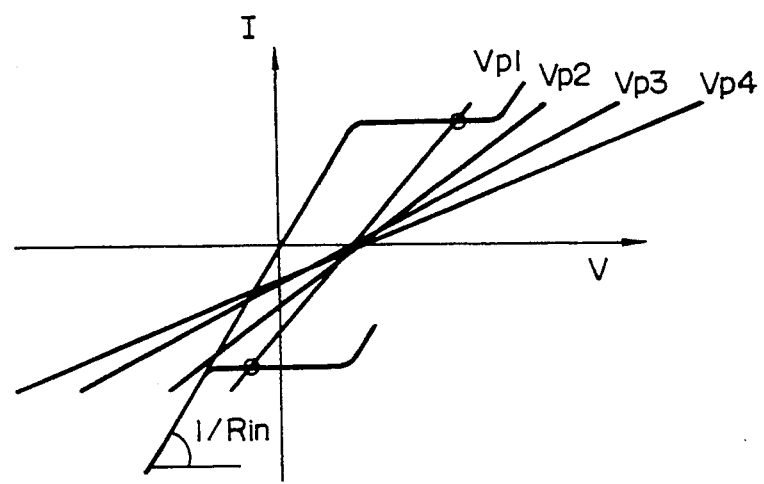
FIG. 20 shows a method for selecting a parameter for obtaining the applied voltage (Vpos) by calculation, starting from the detected internal resistance (Rin) of the oxygen sensor.

Next, the procedure proceeds to Step 332, at which the internal resistance Rin of the oxygen sensor obtained by using the graph indicated in FIG. 19 is outputted. Then, the procedure proceeds to Step 334, at which the parameters r and Ve of the Vpos straight line indicated in FIG. 17 are determined, as indicated in FIG. 20, on the basis of the internal resistance Rin of the oxygen sensor determined at Step 330. The number of Vpos straight lines and the interval therebetween are decided by the precision of determination of the internal resistance Rin. However, as understood from the following Eq. (6), several Vpos straight lines are sufficient;

$$Z1 < Rin \leq Z2 \rightarrow Vp1:Vp = r1 \cdot Ip + Ve1$$
$$Z2 < Rin \leq Z3 \rightarrow Vp2:Vp = r2 \cdot Ip + Ve2$$
$$Z3 < Rin \leq Z4 \rightarrow Vp3:Vp = r3 \cdot Ip + Ve3$$
$$Z4 < Rin \leq Z5 \rightarrow Vp4:Vp = r4 \cdot Ip + Ve4$$
(6)

Even if the internal resistance Rin of the oxygen sensor is varied by changing these Vpos straight lines by changing the internal resistance Rin, Vpos makes a current flow therethrough, which is always in the limit current region, and thus the precision of determination of the air-fuel ratio is secured. Then the procedure proceeds to Step 312, at which Vpos is calculated by using the formula Vpos=ripos+Ve given by Eq. (5) on the basis of r and Ve newly determined at Step 334 and at the succeeding Step 314 it is commanded to apply this voltage Vpos to the oxygen sensor 20.

As described above, even if the internal resistance Rin of the oxygen sensor 20, since the internal resistance Rin at that time is determined and a voltage making a current flow therethrough, which is always in the limit current region, is applied, even if the temperature is varied, the air-fuel ratio can be determined in a large domain of the air-fuel ratio and it can be determined with a high precision. Further, owing to the fact that the current Inega is determined before the current reaches a converged value, after the negative bias Vneg has been applied thereto, a short time of about 30 msec (t11 and t22 in FIG. 5B in the first embodiment described previously being 100 to 200 msec) is sufficient from a determination of the internal resistance Rin of the oxygen sensor 20 to a following determination of the air-fuel ratio and therefore the period of time where the air-fuel ratio cannot be determined can be significantly shortened.

Further there is known a method, by which no Vpos straight line is determined in this third embodiment, as indicate in FIG. 20, but the Vpos straight line is determined, starting from the value of the internal resistance Rin itself, as indicated in JP-B-1-28905. However, by this method, since the internal resistance Rin varies continuously, the Vpos straight line varies also continuously, which makes the number of Vpos straight lines enormous. On the other hand, if data are interpolated in order to reduce the amount of data, the precision of determination of the internal resistance Rin is worsened accordingly and in addition time necessary for determining the internal resistance Rin is elongated. For this reason, when the internal resistance Rin is in a predetermined region, as indicated in FIG. 20, if the Vpos straight line is determined, starting from this region, only several Vpos straight lines are necessary and thus the amount of data for the graph indicated in FIG. 19 can be reduced significantly with respect to that required by the method disclosed in JP-B-1-28905.

Figure 21:
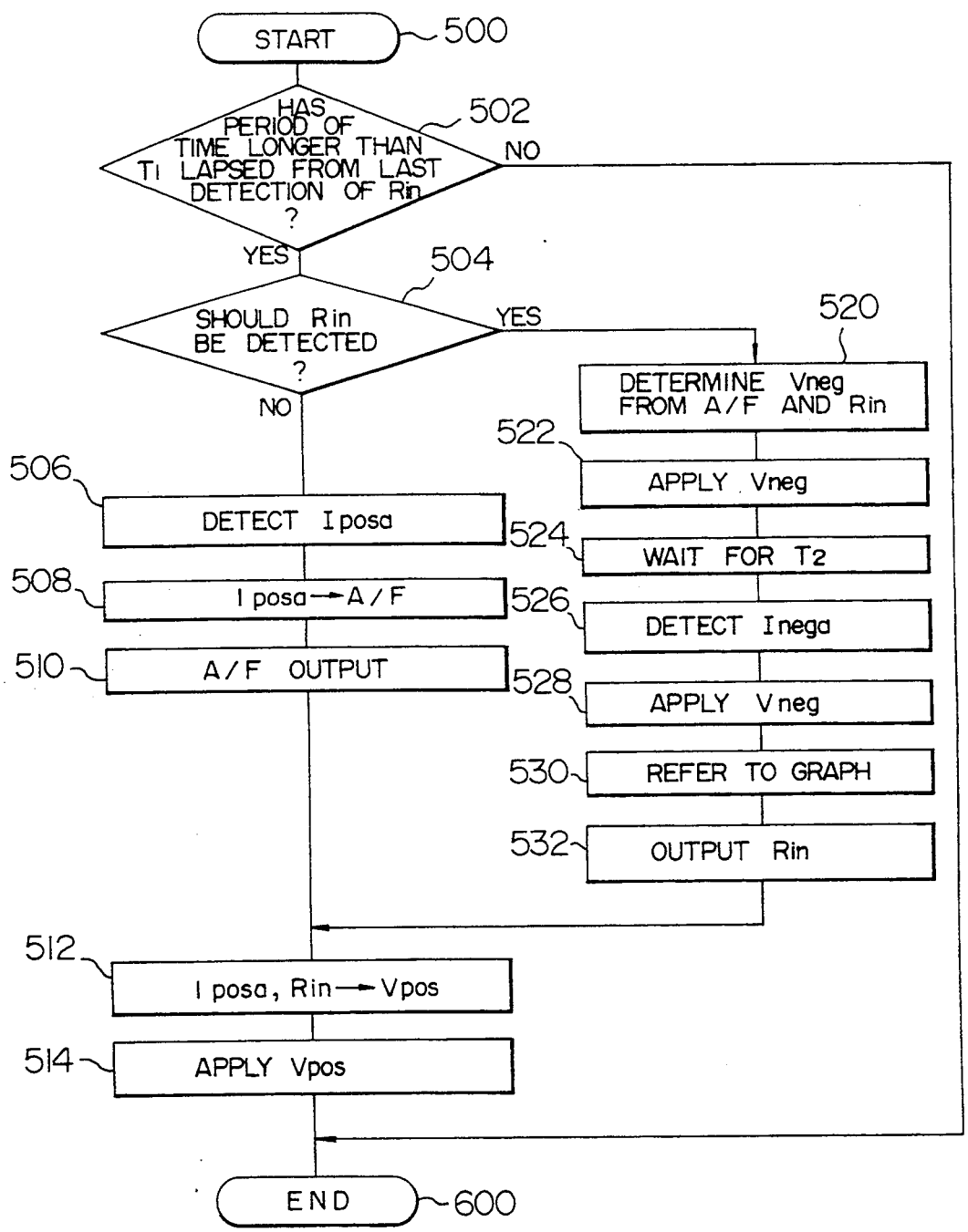
FIG. 21 is a flow chart showing a modified example of the third embodiment.
Figure 22A:
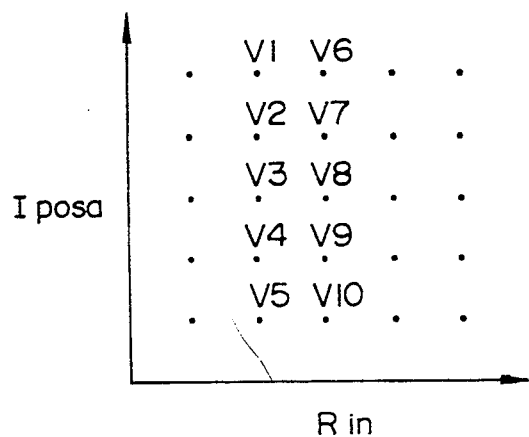
FIGS. 22A and 22B are graphs used for determining the Voltage (Vneg) applied when detecting the internal resistance (Rin) of the oxygen sensor in the modified example of the third embodiment, FIG. 22A being a graph showing the relation among limit current, internal resistance and applied voltage of the oxygen sensor, FIG. 22B being a diagram showing the relation between the applied voltage and the position.
Figure 22B:
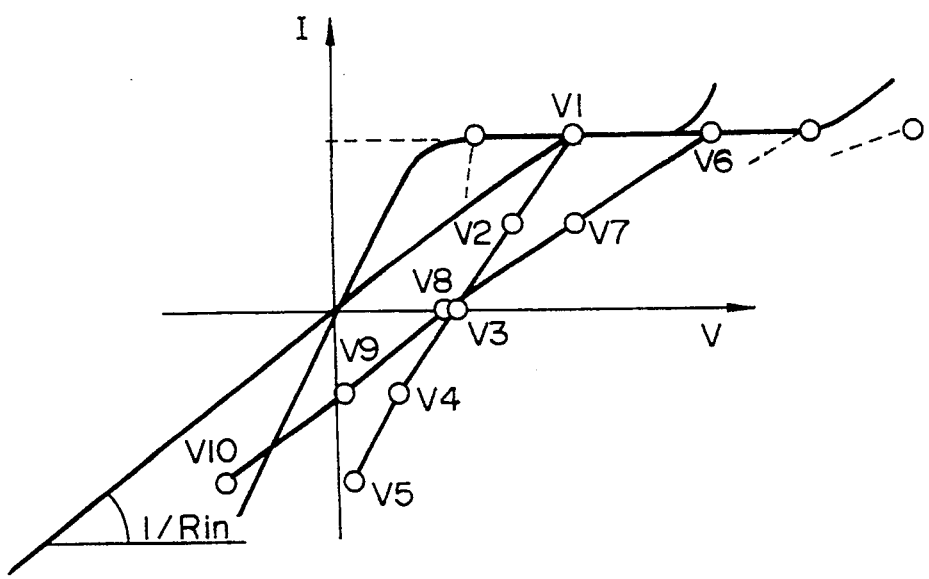

A modified example of the third embodiment described above will be explained, referring to FIGS. 22A and 22B. This modified example differs from the third embodiment described previously in that Vpos is determined, referring to a map, at Step 512 in the flow chart indicated in FIG. 21. That is, while Vpos is obtained by calculation using the formula Vpos=ripos+Ve given by Eq. (5) when obtaining Vpos in the third embodiment, Vpos is determined on the basis of the graph indicated in FIGS. 22A and 22B. If the value of Vpos is obtained by interpolating the internal resistance Rin of the oxygen sensor, although the amount of data for detecting the internal resistance Rin increases, response with respect to variations in the internal resistance is improved.

In execution of the present invention, it is not restricted to determination of oxygen concentration in exhaust gas from the internal combustion engine, but the present invention can be applied to determination of oxygen concentration in various sorts of gas.

We claim:

1. An oxygen concentration measuring device comprising:
   a limit current type oxygen sensor;
   voltage applying means for applying voltage to said oxygen sensor;
   current detecting means for detecting current flowing through said oxygen sensor due to said voltage applied to said oxygen sensor;
   temperature measuring means for measuring temperature of said oxygen sensor based on the detected current; and
   oxygen concentration measuring means for measuring oxygen concentration based on the measured temperature;
   wherein said voltage applying means has negative bias means for negatively biasing said oxygen sensor and said oxygen concentration measuring device further comprises current estimating means for estimating a variation termination value of said current flowing through said oxygen sensor negatively biased by said negative bias means at a point of time in a variation process thereof, and for supplying the variation termination value to said temperature measuring means so that said temperature measuring means uses the variation termination value in place of the detected current.

2. An oxygen concentration measuring device according to claim 1, wherein said current estimating means estimates the variation termination value of said current, starting from:
   current intensity in a variation process of the current flowing through said oxygen sensor under negative bias by said negative biasing means; and
   a transient phenomenon equation representing a relation between said negative bias and variations in said current.

3. An oxygen concentration measuring device according to claim 1, wherein said temperature measuring means obtains the temperature of said oxygen sensor based on a proportional relation between the temperature of said oxygen sensor and the variation termination value of said current flowing through said oxygen sensor negatively biased.

4. An oxygen concentration measuring device according to claim 1, further comprising at least one of time measuring means for measuring time lapsed after the internal combustion engine has been started, means for detecting a fuel supplying state to said internal combustion engine, engine driving state detecting means for detecting driving state of said internal combustion engine, and means for obtaining an amount of variations in the air fuel, said voltage applying means are controlled, based on information coming from that means.

5. An oxygen concentration measuring device according to claim 4, wherein said engine driving state detecting means detects at least one of variations in amount of exhaust gas, number of rotations, amount of sucked air, air intake pipe pressure, temperature of cooling water, throttle aperture and speed of vehicle.

6. An oxygen concentration measuring device according to claim 1, wherein said voltage applying means includes positive bias means for biasing positively said oxygen sensor, and a switching circuit for switching said positive bias means and said negative bias means.

7. An oxygen concentration measuring device according to claim 6, wherein said oxygen concentration is detected by measuring the current flowing through said oxygen sensor under positive bias by said positive bias means.

8. An oxygen concentration measuring device according to claim 1, wherein said oxygen concentration is detected, when it is judged in connection with the measured temperature that said oxygen sensor is approximately in its active state.

9. An oxygen concentration measuring device according to claim 1, further comprising a resistance value control circuit for generating a resistance value corresponding approximately to the internal resistance of said oxygen sensor, said oxygen concentration being detected by controlling said resistance control circuit, based on the measured temperature.

10. An oxygen concentration measuring device according to claim 9, wherein said resistance value control circuit comprises a resistance selecting circuit, with which resistors are connected, a resistance control section for changing connection of said resistance selecting circuit, and a DC power source for applying a positive bias to said resistance selecting circuit.

11. An oxygen concentration measuring device comprising:
   voltage applying means for applying voltage to said oxygen sensor;
   current detecting means for detecting current flowing through said oxygen sensor due to said voltage applied thereto and for obtaining a current level;
   internal resistance determining means for detecting an internal resistance of said oxygen sensor and determining a resistance range, to which said detected internal resistance of said oxygen sensor belongs, from among a plurality of set resistance ranges; and
   voltage determining means for determining a voltage to be applied to said oxygen sensor based on said resistance range determined by said internal resistance determining means and said current level obtained by said current detecting means.

12. An oxygen concentration measuring device according to claim 11, wherein said voltage applying means has negative bias means for supplying negative bias voltage to said oxygen sensor, the internal resistance of said oxygen sensor is obtained by using said negative bias voltage and intensity thus detected of current flowing therethrough due to application of said negative bias voltage.

13. An oxygen concentration measuring device comprising:
   a limit current type oxygen sensor;
   voltage source providing a voltage to said oxygen sensor, said voltage source is used for negatively biasing said oxygen sensor;
   current monitoring device that detects current flowing through said oxygen sensor due to said voltage applied to said oxygen sensor;
   temperature monitoring device that measures a temperature of said oxygen sensor based on said detected current; and
   oxygen concentration measuring device that measures an oxygen concentration based on said measured temperature; and
   current estimating device that estimates a variation termination value of said current flowing through said oxygen sensor negatively biased by said negative bias means at a point of time in a variation process thereof, and for supplying said variation termination value to said temperature measuring means so that said temperature measuring means uses said variation termination value in place of said detected current.

* * * * *